United States Patent
Boyd et al.

(10) Patent No.: US 6,575,981 B1
(45) Date of Patent: Jun. 10, 2003

(54) METHODS AND INSTRUMENTATION FOR VERTEBRAL INTERBODY FUSION

(75) Inventors: Lawrence M. Boyd, Memphis, TN (US); Eddie F. Ray, Cordova, TN (US); Bradley T. Estes, Memphis, TN (US); J. Kenneth Burkus, Columbus, GA (US); John D. Dorchak, Midland, GA (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/498,426

(22) Filed: Feb. 4, 2000

Related U.S. Application Data

(60) Provisional application No. 60/118,793, filed on Feb. 4, 1999.

(51) Int. Cl.[7] ................................................ A61B 17/56
(52) U.S. Cl. .......................................................... 606/90
(58) Field of Search ........................... 606/90, 99, 105; 623/17.11, 17.16

(56) References Cited

U.S. PATENT DOCUMENTS

| | | |
|---|---|---|
| 5,015,255 A | 5/1991 | Kuslich |
| 5,055,104 A | 10/1991 | Ray |
| 5,431,658 A | 7/1995 | Moskovich |
| 5,484,437 A | 1/1996 | Michelson |
| 5,489,307 A | 2/1996 | Kuslich et al. |
| 5,505,732 A | 4/1996 | Michelson |
| 5,514,180 A | 5/1996 | Heggeness et al. |

(List continued on next page.)

FOREIGN PATENT DOCUMENTS

| | | |
|---|---|---|
| EP | 0 732 093 A2 | 2/1996 |
| EP | 0 880 938 A1 | 12/1998 |
| WO | WO 93/14801 | 8/1993 |
| WO | WO 96/27345 | 9/1996 |
| WO | WO 96/40020 | 12/1996 |
| WO | WO 99/09896 | 3/1999 |
| WO | WO 99/09913 | 3/1999 |
| WO | WO 99/52453 | 10/1999 |
| WO | WO 99/59481 | 11/1999 |
| WO | WO 00/041654 | 7/2000 |
| WO | WO 00/041655 | 7/2000 |

OTHER PUBLICATIONS

*Surgical Technique Using Bone Dowel Instrumentation for Anterior Approach*, Sofamor Danek The Spine Specialist, 1996.
*Reduced Profile Instrumentation Surgical Technique*, as described by J. Kenneth Burkus and John D. Dorchak, M.D.; Sofamor Danek, © 1999.
*Anterior Instrumentation Surgical Technique*, as described by Scott H. Kitchel, M.D.; Sofamor Danek, © 1999.

*Primary Examiner*—Eduardo C. Robert
(74) *Attorney, Agent, or Firm*—Woodard, Emhardt, Moriarty, McNett & Henry LLP

(57) ABSTRACT

A method and instrumentation particularly adapted for disc space preparation from an anterior approach to the spine. The invention provides an improved guide sleeve defining a channel having overlapping cylindrical working channel portions and lateral non-distracting extensions extending from reduced thickness wall portions. The guide sleeve has an overall reduced width configuration adjacent the distal end due to the overlapping working channel portions and reduced thickness wall portions. A pair of distractors are provided. A first distractor includes a shaft and distal tip, each having convex walls. A second distractor includes a shaft and distal tip including a recessed area at least along the tip. The first distractor is at least partially received within the recessed area of the second distractor when the first and second distractors are in side-by-side relation and a reduced overall width of the distractors is obtained. Preferably, the first and second distractors are used with the guide sleeve. A method of using the disclosed instruments is also provided.

32 Claims, 18 Drawing Sheets

OTHER PUBLICATIONS

| | | | |
|---|---|---|---|
| 5,556,399 A | 9/1996 | Huebner |
| 5,569,205 A | 10/1996 | Hart et al. |
| 5,571,109 A | 11/1996 | Bertagnoli |
| 5,609,636 A | 3/1997 | Kohrs et al. |
| 5,720,748 A | 2/1998 | Kuslich et al. |
| 5,741,253 A | 4/1998 | Michelson |
| 5,759,185 A | 6/1998 | Grinberg |
| 5,766,252 A | 6/1998 | Henry et al. |
| 5,772,661 A | 6/1998 | Michelson |
| 5,785,710 A | 7/1998 | Michelson |
| 5,797,909 A | 8/1998 | Michelson |
| 5,865,834 A | 2/1999 | McGuire |
| 5,865,847 A | 2/1999 | Kohrs et al. |
| 5,885,299 A | 3/1999 | Winslow et al. |
| 5,899,908 A | 5/1999 | Kuslich et al. |
| 5,947,971 A | 9/1999 | Kuslich et al. |
| 5,968,098 A | 10/1999 | Winslow |
| 6,004,326 A | 12/1999 | Castro et al. |
| 6,033,405 A | 3/2000 | Winslow et al. |
| 6,042,582 A | 3/2000 | Ray |
| 6,056,749 A | 5/2000 | Kuslich |
| 6,059,790 A | 5/2000 | Sand et al. |
| 6,063,088 A | 5/2000 | Winslow |
| 6,080,155 A | 6/2000 | Michelson |
| 6,083,225 A | 7/2000 | Winslow et al. |
| 6,086,595 A | 7/2000 | Yonemura et al. |
| 6,096,038 A | 8/2000 | Michelson |
| 6,113,602 A | 9/2000 | Sand |
| 6,120,506 A | 9/2000 | Kohrs et al. |
| 6,123,705 A | 9/2000 | Michelson |
| 6,156,595 A | 12/2000 | Yonemura et al. |
| 6,159,214 A | 12/2000 | Michelson |
| 6,171,339 B1 | 1/2001 | Houfburg et al. |
| 6,174,311 B1 | 1/2001 | Branch et al. |
| 6,210,412 B1 | 4/2001 | Michelson |
| 6,224,595 B1 | 5/2001 | Michelson |
| 6,224,599 B1 | 5/2001 | Baynham |
| 6,224,607 B1 | 5/2001 | Michelson |
| 2001/0016741 A1 * | 8/2001 | Burkus et al. ................ 606/57 |

* cited by examiner

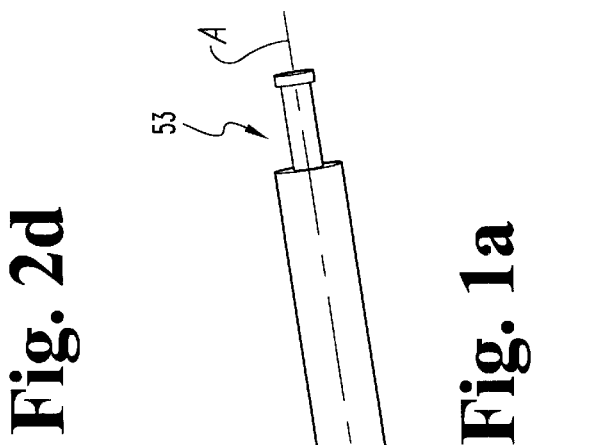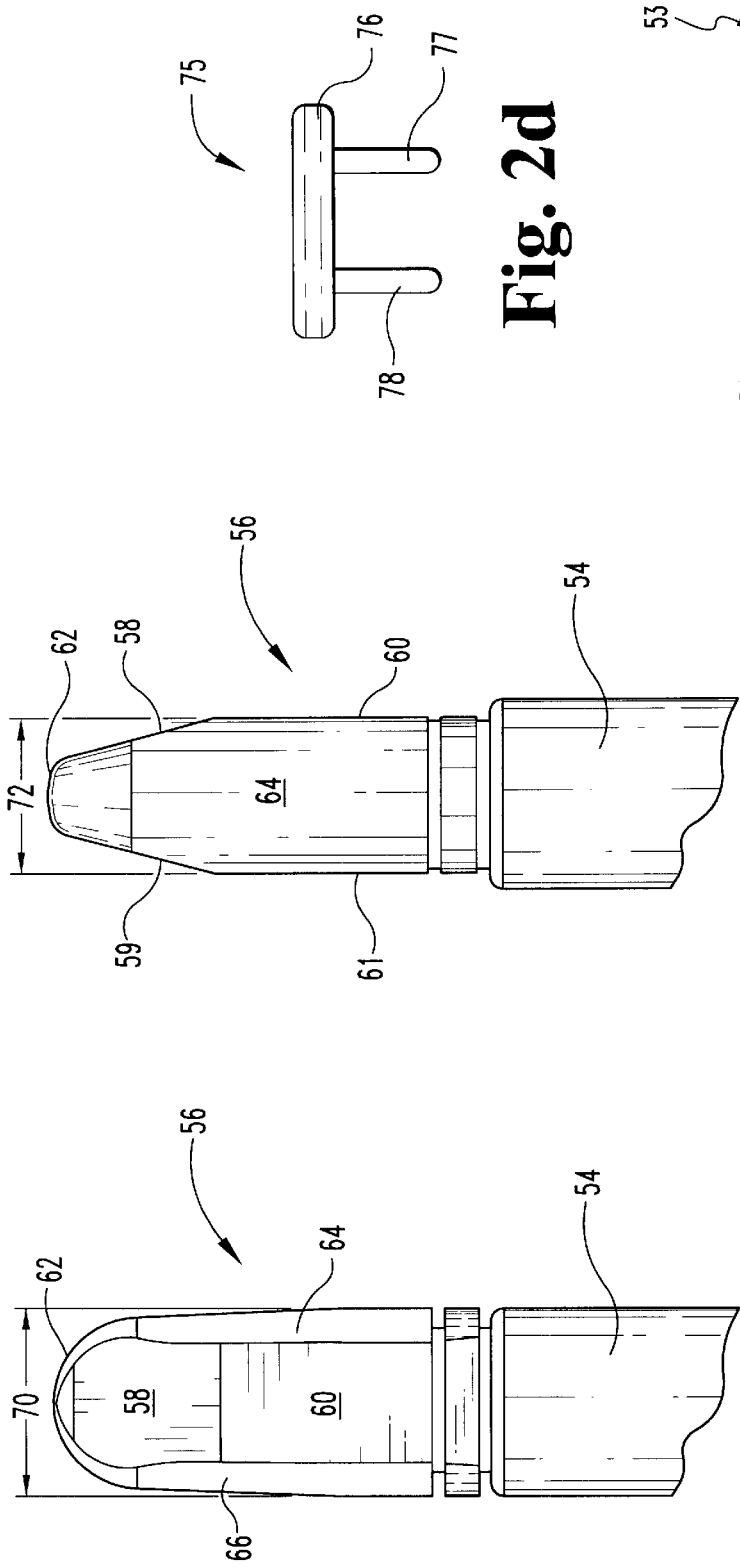

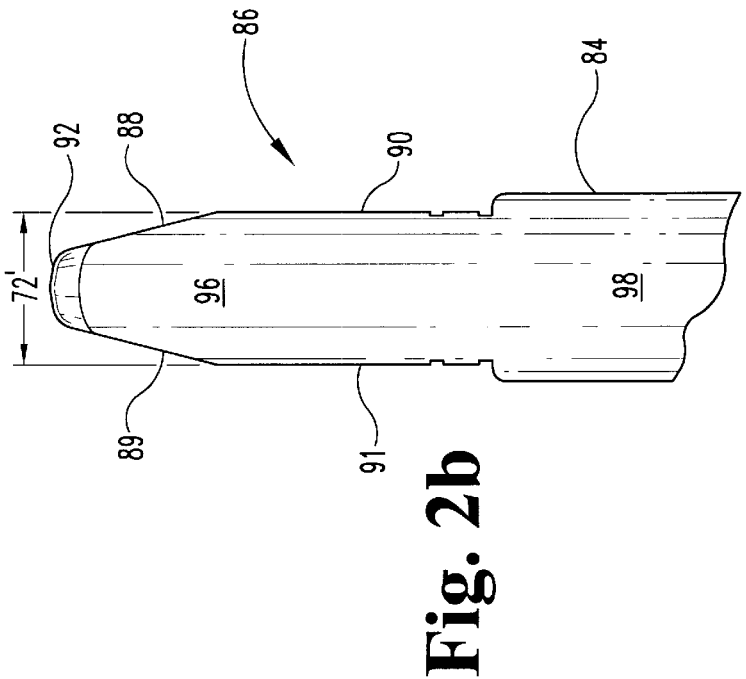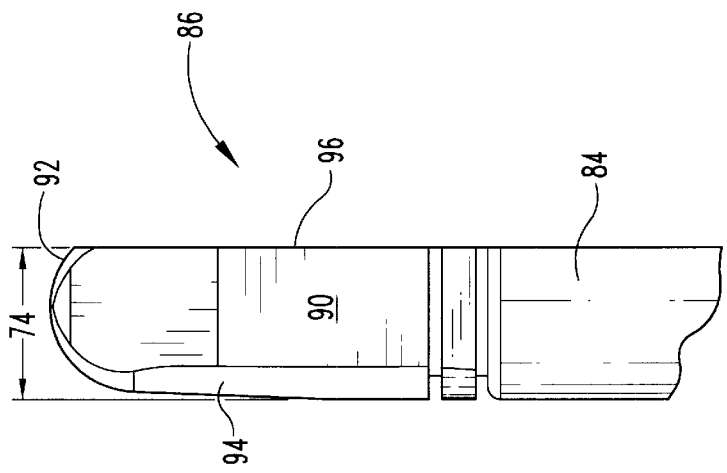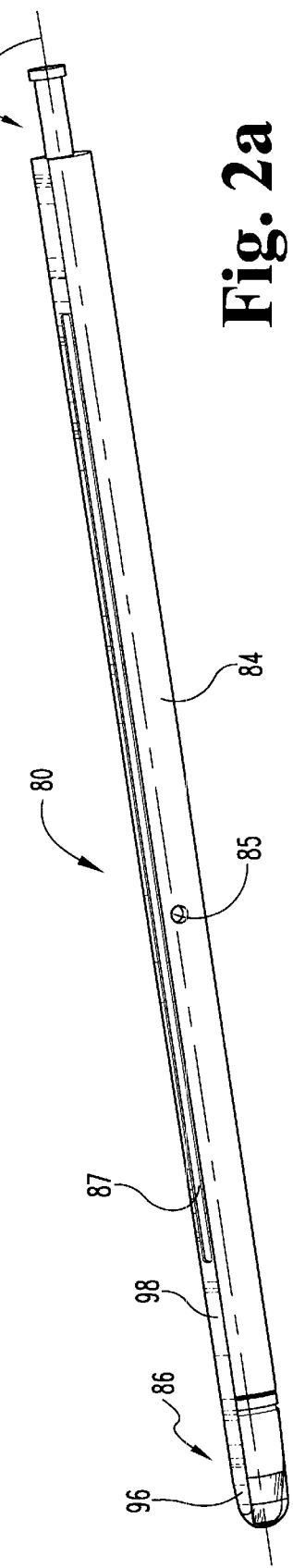

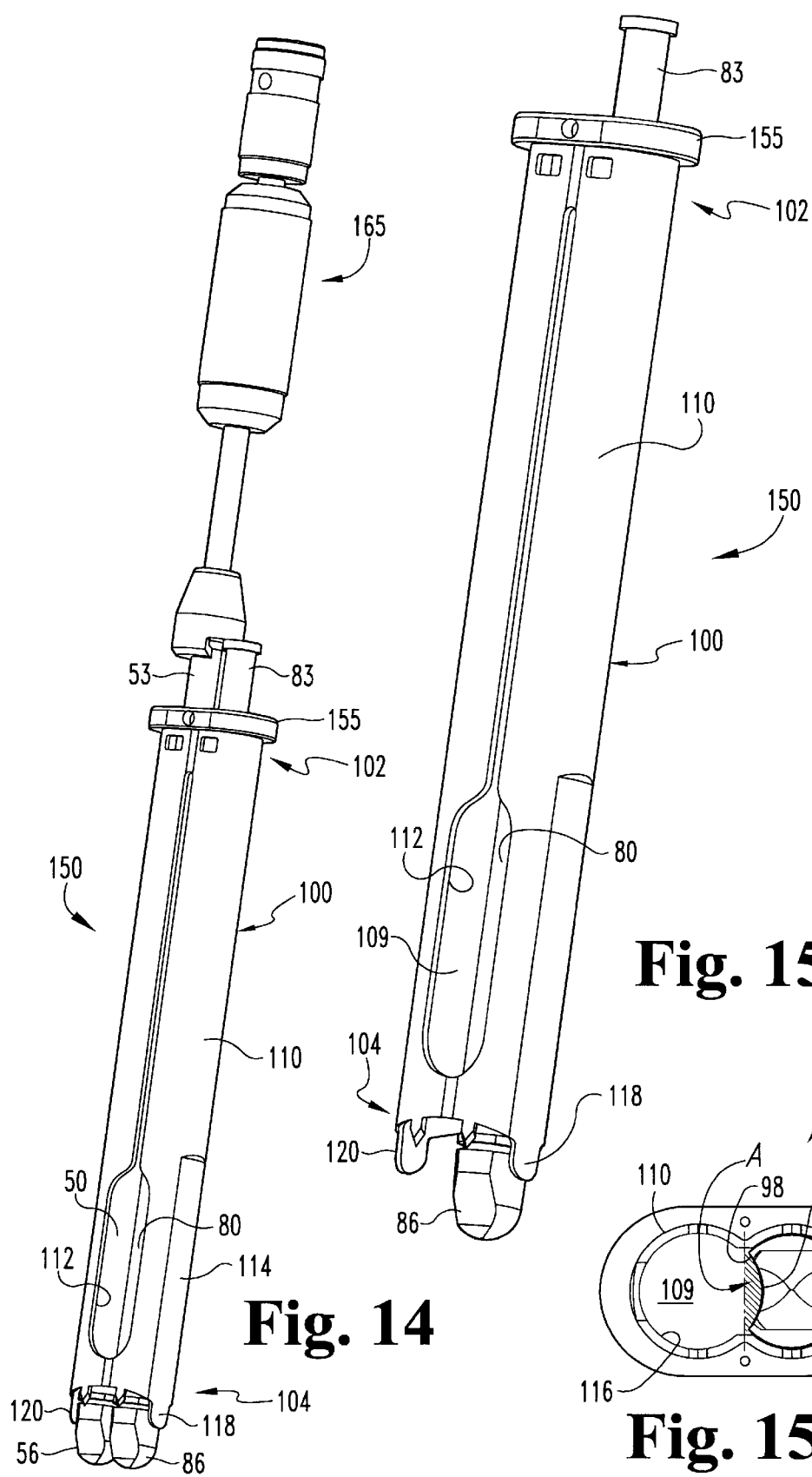
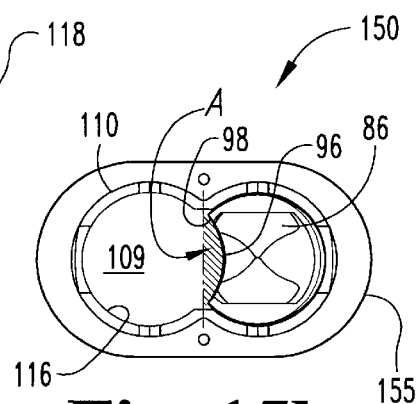
Fig. 14
Fig. 15a
Fig. 15b

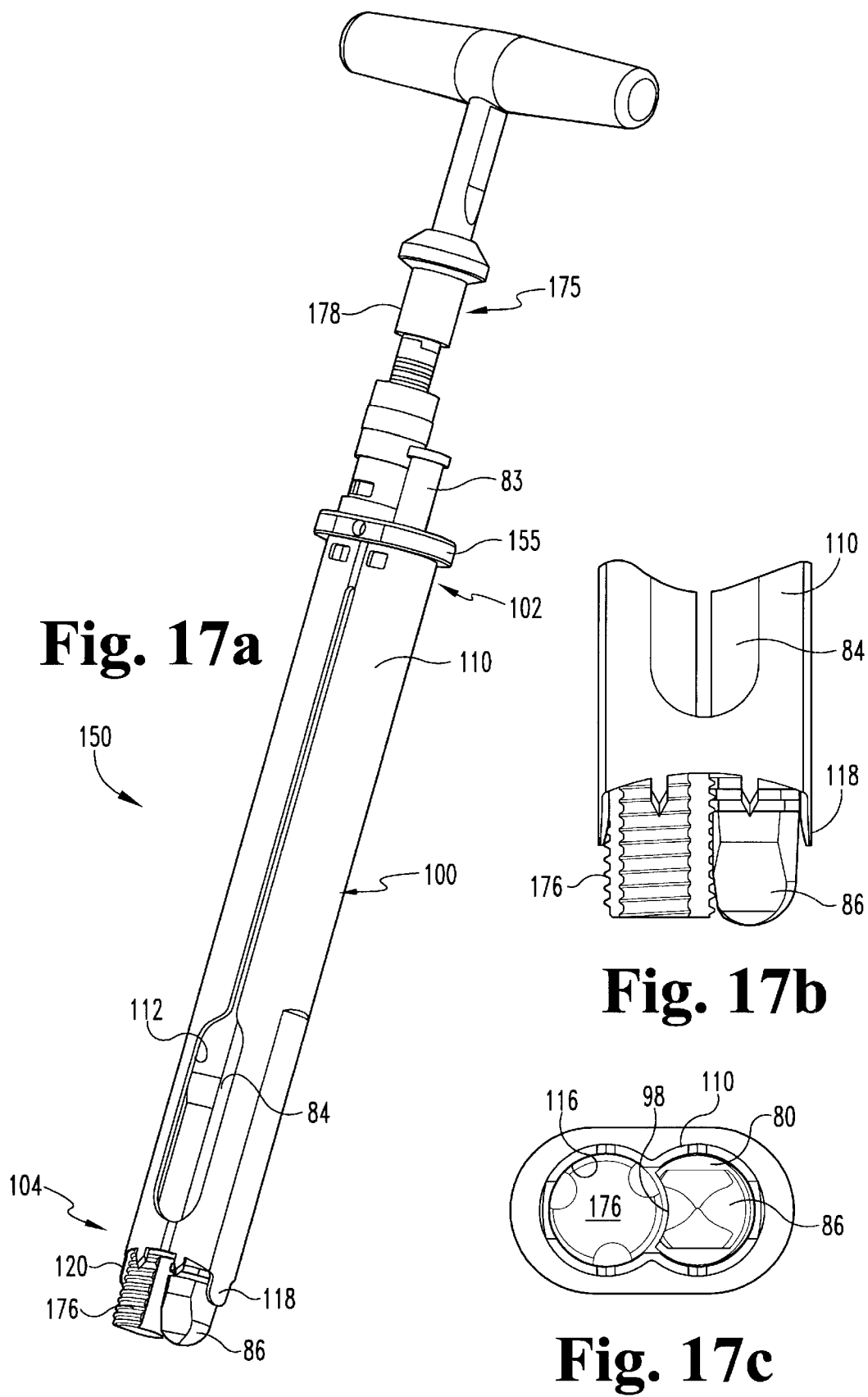
Fig. 17a
Fig. 17b
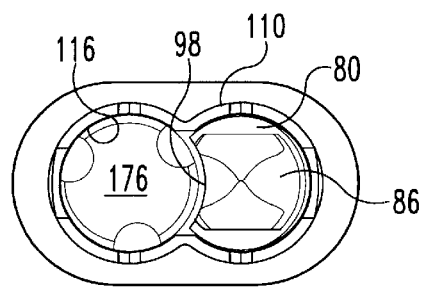
Fig. 17c

METHODS AND INSTRUMENTATION FOR VERTEBRAL INTERBODY FUSION

CROSS-REFERENCE TO RELATED APPLICATIONS

The present application claims the benefit of the filing date of Provisional application Ser. No. 60/118,793, filed Feb. 4, 1999, entitled METHOD AND INSTRUMENTATION FOR INTERBODY FUSION. The referenced application is incorporated herein by reference in its entirety.

BACKGROUND OF THE INVENTION

The present invention relates generally to surgical procedures for spinal stabilization and more specifically to instrumentation adapted for inserting a spinal implant within the intervertebral disc space between adjacent vertebra. More particularly, while aspects of the invention may have other applications, the present invention is especially suited for disc space preparation and implant insertion into a disc space from an anterior surgical approach to the spine.

Various surgical methods have been devised for the implantation of fusion devices into the disc space. Both anterior and posterior surgical approaches have been used for interbody fusions. In 1956, Ralph Cloward developed a method and instrumentation for anterior spinal interbody fusion of the cervical spine. Cloward surgically removed the disc material and placed a tubular drill guide with a large foot plate and prongs over an alignment rod and then embedded the prongs into adjacent vertebrae. The drill guide served to maintain the alignment of the vertebrae and facilitated the reaming out of bone material adjacent the disc space. The reaming process created a bore to accommodate a bone dowel implant. The drill guide was thereafter removed following the reaming process to allow for the passage of the bone dowel which had an outer diameter significantly larger than the reamed bore and the inner diameter of the drill guide. The removal of the drill guide left the dowel insertion phase completely unprotected.

More recent techniques have advanced this concept and have provided further protection for sensitive tissue during disc space preparation and dowel insertion. Such techniques have been applied to an anterior approach to the lumbar spine.

An initial opening or openings are made in the disc space and the height of the disc space is distracted to approximate normal height. Typically, a first distractor is inserted with a height estimated by radiological examination. If additional distraction is required, the first distractor is removed and a second, larger distractor is inserted. However, since the positioning of the distractors is performed without the benefit of protective guide sleeves, the switching of distractors increases the potential for damage to neutovascular structures and may correspondingly increase the time of the procedure.

For bilateral procedures, a double barrel sleeve may be inserted over the distractors, with a central extension extending into the disc space to maintain distraction. One limitation on guide sleeve placement is the amount of neurovascular retraction that must be achieved to place the guide sleeves against the disc space. For some patients, a double barrel sleeve may not be used because there is insufficient space adjacent the disc space to accept the sleeve assembly. Thus, there remains a need for guide sleeves requiring less neurovascular retraction for proper placement and providing greater protection to adjacent tissue.

While the above-described techniques are advances, improvement is still needed to reduce the procedure time by utilization of improved instruments and techniques, to reduce the potential for damage to sensitive tissue adjacent the disc space, and to limit the amount of vessel retraction necessary to utilize the protective instrumentation. The present invention is directed to this need and provides more effective methods and instrumentation for achieving the same.

SUMMARY OF THE INVENTION

The present invention relates to methods and instrumentation for vertebral interbody fusion. In one aspect of the invention, the instruments define a reduced width configuration that allows bilateral insertion of implants into the disc space.

In one aspect of the invention, a distractor is provided that includes a distractor shaft with a length. A distractor tip extends from on end of the shaft. The distractor tip has opposite first and second surfaces that define a distraction height between the surfaces. The distractor tip has a recessed area, preferably a concave surface, that extends between the first and second surfaces. Optionally, the distractor shaft may include a recessed area along its length that is an extension of the recessed area of the distractor tip. The recessed area of the distractor and/or shaft may permit the passage of and rotation of surgical devices adjacent thereto.

In another aspect of the present invention, a guide sleeve has a wall that defines a protected passageway to a distracted disc space. The guide sleeve includes a proximal end and a distal end. A pair of overlapping working channels extends between the ends. The sleeve has a first width at the proximal end and a second width at the distal end. The first width is greater than the second width. The reduced second width is provided by reducing the exterior wall thickness of the sleeve at the distal end. Preferably, a first flange and a second flange extend from the distal end at the reduced wall thickness portions. Preferably, the flanges have a thickness that corresponds to the reduced wall thickness. Still more preferably, the first and second lateral extensions have a height less than the height of the distracted disc space, and inhibit encroachment of adjacent tissue into the distracted disc space. In another form, the guide sleeve may include spikes projecting from the sleeve distal end between the flanges to engage the adjacent vertebral bodies. In a further form, the overlapping working channels are substantially cylindrical.

In another aspect, there is provided a guide sleeve assembly. The assembly includes a sleeve defining a working channel. A first distractor has a first distractor tip with a recessed area along a portion of its length, and a second distractor has a second distractor tip. With the first distractor disposed in the working channel of the sleeve in side-by-side relation with the second distractor, the recessed surface of the first distractor tip receives at least a portion of the second distractor tip. In one form, the recessed area of the first distractor tip is defined by a concave surface and the second distractor tip has opposite convex surfaces, one of which is positioned adjacent the concave surface of the first distractor tip. In another form, the first and second distractors define an overlap region in the guide sleeve working channel.

In a method according to the present invention, access is gained to a disc space. A first distractor having first distractor tip with a recessed area and a second concave distractor having a second distractor tip are disposed in side-by-side relation with the distractor tips inserted adjacent the disc space. Preferably, the distractors are also engaged within the working channel of an outer sleeve. The distractors distract and maintain the disc space at the desired height during the procedure. Once the desired distraction of the disc space has been achieved, the outer sleeve is advanced toward the disc space until disposed adjacent the disc space. If necessary, a driving cap may be positioned over the proximal end of the outer sleeve to apply a driving force thereto.

The outer sleeve is then driven into position so that opposing side flanges are positioned in the disc space and spikes on the outer sleeve enter the vertebral bodies. Preferably, the side flanges do not perform any distraction of the disc space. Once the outer sleeve is positioned, the second distractor may be removed and a substantially cylindrical working space is provided through the sleeve to the disc space adjacent the first distractor. Preferably, the working space defines an area that is greater than one half of the area of the working channel of the guide sleeve.

Various surgical procedures are performed through the working space, such as reaming, tapping and inserting a threaded implant into the disc space. Once the first implant is inserted, the second distractor is removed, and the first implant maintains the disc space distraction and defines a working space adjacent the inserted implant. Preferably, the first implant has a concave side wall to define a portion of a substantially cylindrical working space. The surgical procedures are then repeated to insert a second implant adjacent the first implant. In one embodiment, the second implant has a circular cross-section. In another embodiment, the implant has a cross-section that mirrors that of the first implant after insertion.

Although various sleeves are known in the art, in a preferred embodiment, outer sleeves according to the present invention have a reduced width portion adjacent the bone engaging distal end to limit the amount of retraction of the surrounding vasculature and neural tissue required for the procedure. The reduced width portion, preferably in combination with the previously described overlapping working channels, combine to greatly reduce the overall width of the sleeve. In a preferred form, a sleeve assembly includes a pair of opposite side flanges or lateral extensions having a first height. The lateral extensions provide protection from encroachment of tissue into the working area of the disc space. Preferably, the side flanges of the outer sleeve are not used to maintain distraction of the disc space and thus do not experience the forces of disc space distraction. As a result, the flanges and adjacent side walls may be formed with a reduced wall thickness.

A further aspect includes the provision of a visualization window along the centerline of the outer sleeve for visual access to the interior working channel while instruments are in the working channel. Even without the use of an imaging system, the present invention contemplates the use of manually adjustable depth stop that is to control the steps of trephining, reaming, tapping, and implant insertion. The term implant is used in a broad sense throughout the disclosure and is intended to encompass bone dowels, metallic cages and spacers, and other implants used for interbody fusion regardless of shape or material of construction.

Related objects, advantages, aspects, forms, and features of the present invention will be apparent from the following description.

DESCRIPTION OF THE DRAWINGS

FIG. 1a is a perspective view of a distractor according to the present invention.

FIG. 1b is an enlarged front view of the tip of the distractor of FIG. 1a.

FIG. 1c is an enlarged side view of the tip of the distractor of FIG. 1a.

FIG. 2a is a perspective view of a distractor according to another aspect of the present invention.

FIG. 2b is an enlarged front view of the tip of the distractor of FIG. 2a.

FIG. 2c is an enlarged side view of the tip of the distractor of FIG. 2a.

FIG. 2d is an elevation view of a distractor clip.

FIG. 14 is a perspective view of the guide sleeve assembly with a slap hammer disposed on one of the distractors.

FIGS. 15a–15b are a perspective view and an end view, respectively, of the guide sleeve assembly with a distractor removed.

FIGS. 17a–17c are a perspective view, detail view and end view, respectively, of the guide sleeve assembly with a tap disposed adjacent a distractor.

DESCRIPTION OF THE PREFERRED EMBODIMENTS

Figure 3:
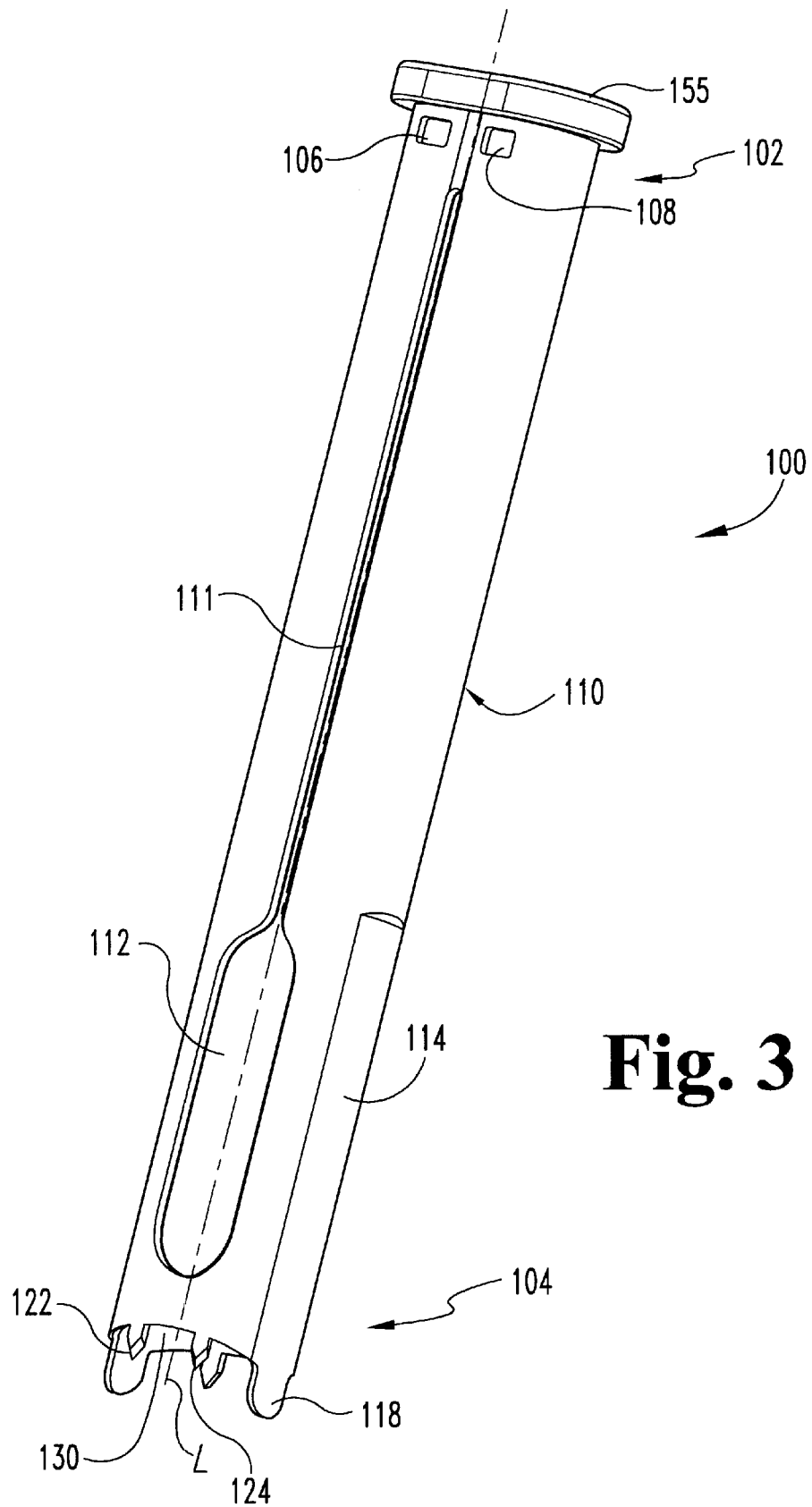
FIG. 3 is a perspective view of a guide sleeve according to another aspect of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to methods and instrumentation for performing vertebral interbody fusion. Specifically, although aspects of the present invention may have other uses either alone or in combination, the instruments and methods disclosed herein are particularly useful for anterior lumbar interbody fusion. However, the surgical instruments and methods according to the present invention are not limited to such an approach, and may find application in, but without limitation, lateral and anterior-lateral approaches to the spine as well. Also, the surgical instruments and methods of the present invention may find application at all vertebral segments of the spine, and in areas other than spinal surgery.

Referring now to FIGS. 1a–c, there is shown a convex or first disc space distractor 50 according to one aspect of the present invention. Distractor 50 includes a proximal end 53 configured for engagement with conventional tools and handles (not shown) used in operative procedures on the spine. A shaft 54 is joined with a distractor tip 56. In the illustrated embodiment, shaft 54 has a hollow interior and a clip hole 55 communicating with the hollow interior; however, the present invention also contemplates a solid shaft 54. Also, while an integral shaft and head are shown, head 56 may be removably attached to shaft 54. One such removable attachment is more fully disclosed in U.S. Patent Application entitled METHOD AND INSTRUMENTATION FOR VERTEBRAL INTERBODY FUSION, Ser. No. 09/287,917, filed Apr. 7, 1999, which is incorporated herein by reference in its entirety (hereinafter referred to as the '917 patent application.) Distractor tip 56 is designed such that it can be inserted in a disc space to establish a first working distraction height 72 (see FIG. 1b). More specifically, distractor tip 56 has a rounded leading edge 62 that extends to opposing inclined surfaces 58 and 59, which in turn extend more proximally and blend into substantially planar opposing surfaces 60 and 61, respectively. Extending between planar surfaces 60 and 61 and proximal the rounded tip 62 are opposite convex surfaces 64 and 66.

Planar surfaces 60 and 61 extend in a substantially parallel alignment along a longitudinal axis A of distractor 50 and define height 72 therebetween It should be understood that the inclined surfaces 58 and 59 cooperate to aid insertion of the distractor tip 56 into the disc space and to initially distract the disc space to at least a height 72. If first distraction height 72 is sufficient, further procedures as known in the art may then be carried out to accomplish implant insertion. While a specific distractor has been described in detail, it is contemplated that other known distractor configurations may be substituted for the same without deviating from the scope of this invention.

Referring now to FIGS. 2a–c, there is shown a second disc space distractor 80 according to one aspect of the present invention. Distractor 80 includes a proximal end 83 configured for engagement with conventional tools and handles (not shown). A shaft 84 is joined with a distractor tip 86. In the illustrated embodiment, shaft 84 has a hollow interior and a hole 85 communicating therewith. While an integral shaft and head are shown tip 86 may be removably attached to shaft 84, as similarly described with respect to the removable attachments disclosed in the '917 patent application. Similar to distractor tip 56 of distractor 50, distractor tip 86 is designed such that it can be inserted in a disc space to establish a first working distraction height 72' (see FIG. 2b) that is preferably the substantially the same as working height 72. More specifically, distractor tip 86 has a rounded leading edge 92 that extends to opposing inclined surfaces 88 and 89 which, in turn, extend more proximally and blend into substantially planar opposing surfaces 90 and 91, respectively.

Planar surfaces 90 and 91 extend substantially parallel to longitudinal axis B of distractor 80 to define height 72' therebetween. Extending between planar surfaces 90 and 91 are convex surface 94 and a recessed area defined by opposite concave surface 96. Along the distractor shaft 84, there is defined a concave surface 98 that is adjacent to and coplanar with concave surface 96 of distal tip 86 to define a concave surface extending along the length of distractor 80. In the illustrated embodiment, Surface 98 has a slot 87 formed therein communicating with the hollow interior of shaft 84; however, it the present invention also contemplates a solid shaft 84 and a shaft 84 without slot 87. As explained more fully below, concave surfaces 96, 98 are configured to receive convex surface 64 or 66 of distractor 50 to reside therein when distractors 50 and 80 are disposed in side-by-side relation. Concave surfaces 96, 98 also partially define a working space that allows operative procedures to be performed therethrough.

It should be understood that the inclined surfaces 88 and 89 cooperate to aid insertion of distractor tip 86 into the disc space, and to distract the disc space and maintain disc space distraction to at least a height 72, 72'. To further aid in distractor insertion, in FIG. 2d there is shown a distractor clip 75 having a cross member 76 with first clip member 77 and second clip member 78 extending therefrom. Clip members 77 and 78 are each received in a corresponding one of holes 55 and 85 to couple distractor 50 to distractor 80. Clip 75 prevents splaying and maintains the relative positioning of distractors 50, 80 during insertion into the disc space. If first distraction height 72 is sufficient, further procedures as known in the art may then be carried out to accomplish implant insertion. It should be further understood that second distractor 80 has a second width 74 that is less than a first width 70 of first distractor 50.

Specifically, but without limitation, the distractor heads 56, 86 may be formed with heights 72 ranging from 6 mm to 24 mm. Preferably, height 72 of the next sized distractor increases or decreases in 2 mm increments. Other variations and may be provided as long as the working distractor height provided approximates the disc height in a normal spine and accommodates insertion of an implant into the disc space as more fully described below.

Referring now to FIG. 3, there is shown a guide sleeve 100 that is useful with the distractors 50 and 80 described above. Guide sleeve 100 has a wall 110 defining a working channel 130 having a figure eight shaped cross-section (FIG. 9) extending in a substantially unobstructed manner from a proximal end 102 to a distal end 104. Sleeve 100 includes upper windows 106 and 108 formed in wall 110 on at least one side of sleeve 100 for engagement by a removal tool to remove sleeve 100. The sleeve 100 also includes lower elongated visualization window 112 centered about the longitudinal axis L with an elongated slot 111 extending proximally window 12. Window 112 provides the surgeon with the ability to visualize the instruments inserted in guide sleeve 100 as well as the openings in the disc space and vertebral bodies, without entirely removing instrumentation from guide sleeve 100. The reduce width of sleeve 100 allows the use of one window 112 for visualization of implant insertion into its respective bilateral location in the disc space, and separate windows along each insertion path are not necessary. However, it should be understood that any number of visualization windows and configurations thereof are contemplated herein, such as those described in the '917 patent application. The present invention also contemplates that covers may be used for visualization windows, as described in greater detail in the '917 patent application.

At proximal end 102 is provided a flange ring 155. Flange ring 155 strengthens sleeve 100 and provides a load transfer member to facilitate transfer of a driving force to sleeve 100, as described more fully below. Adjacent distal end 104, the material thickness along the exterior outer edge of wall 110 is reduced in order to provide a reduced thickness wall portion 114 and an opposite reduced thickness wall portion (not shown). The reduced thickness wall portions define a smaller cross-sectional area for the sleeve 100 as well as a reduced width extending transverse to the longitudinal axis L. The reduced cross-sectional area and smaller width of guide sleeve 100 reduces the amount of vasculature and neural tissue retraction adjacent the disc space that would otherwise be required to place a similarly sized guide sleeve without the width reduction.

Figure 7:
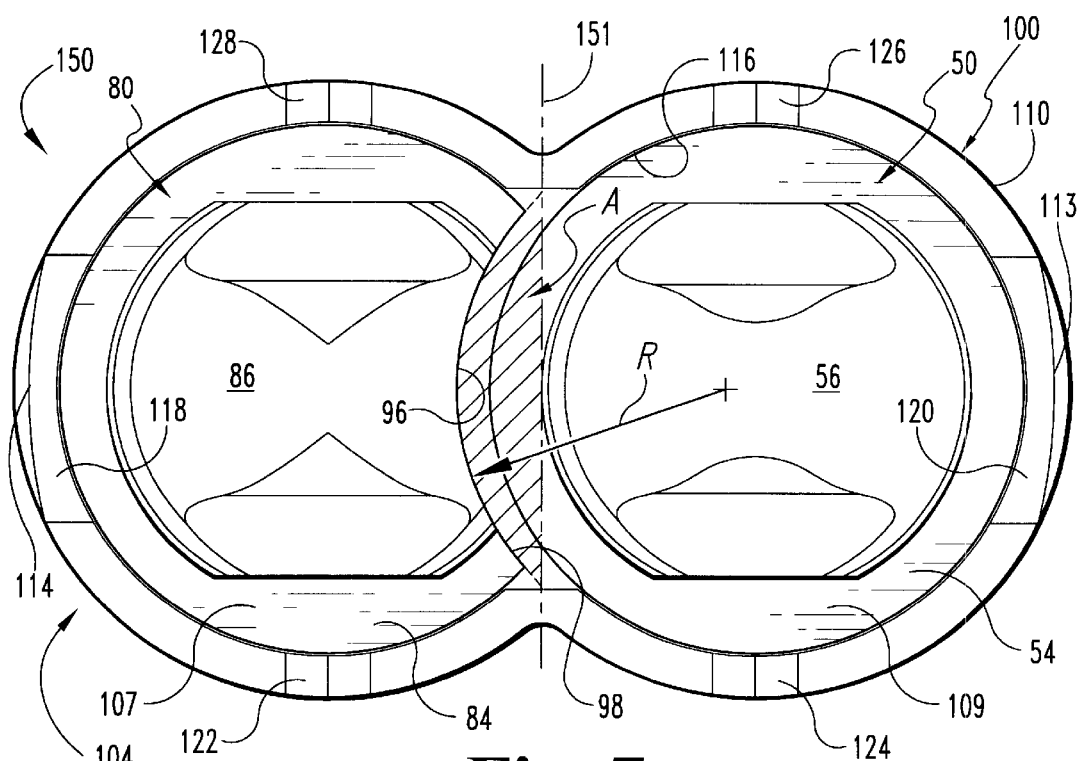
FIG. 7 is an enlarged end view of the distal end of the guide sleeve assembly of FIG. 6.

Distal end 104 includes a pair of flanges 118 and 120 extending from wall 110 on opposite sides of working channel 130. Flanges 118 and 120 are configured to extend partially into the disc space. Flanges 118, 120 are each formed by and are an extension of the corresponding reduced thickness wall portions 114 described above. In a preferred embodiment, flanges 118 and 120 do not provide distraction of the disc space but are primarily provided to protect surrounding vessels and neurological structures from damage during the procedures. Since the lateral flanges do not provide structural support for distraction, the material thickness of the flanges and adjacent side walls may be reduced. Additionally, distal end 104 includes spikes 122, 124, positioned between flanges 118, 120 and a third spike 126 and a fourth spike 128 positioned opposite spikes 122, 124 between flanges 118, 120 as shown in FIG. 7. These spikes may be urged into the bone of the adjacent vertebral bodies to hold guide sleeve 100 in a fixed position relative to the vertebral bodies.

Figure 4:
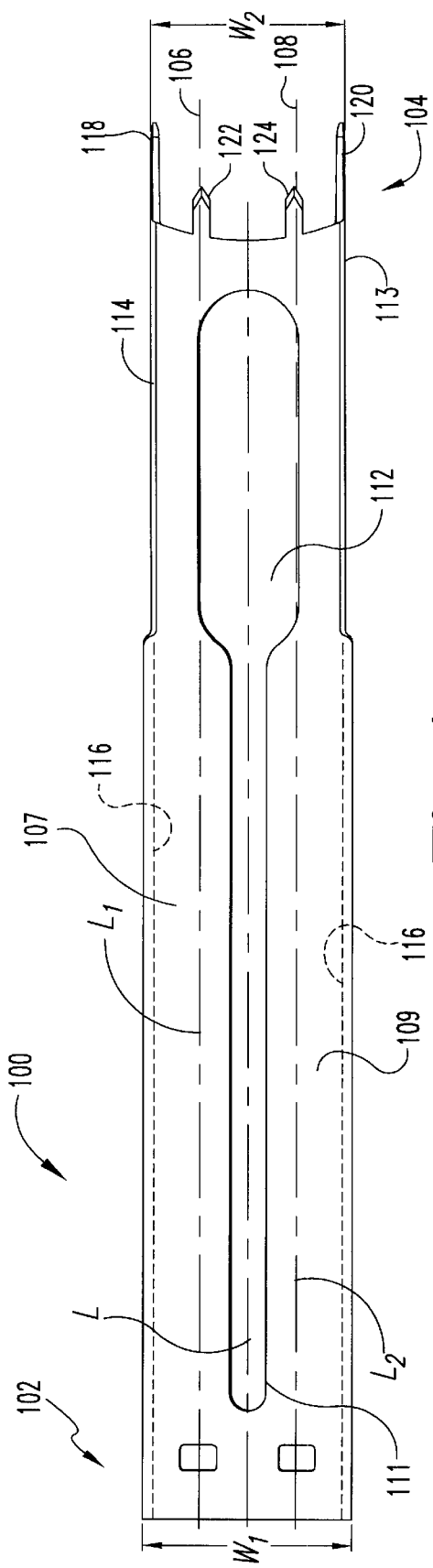
FIG. 4 is a front view of the guide sleeve of FIG. 3.
Figure 5:
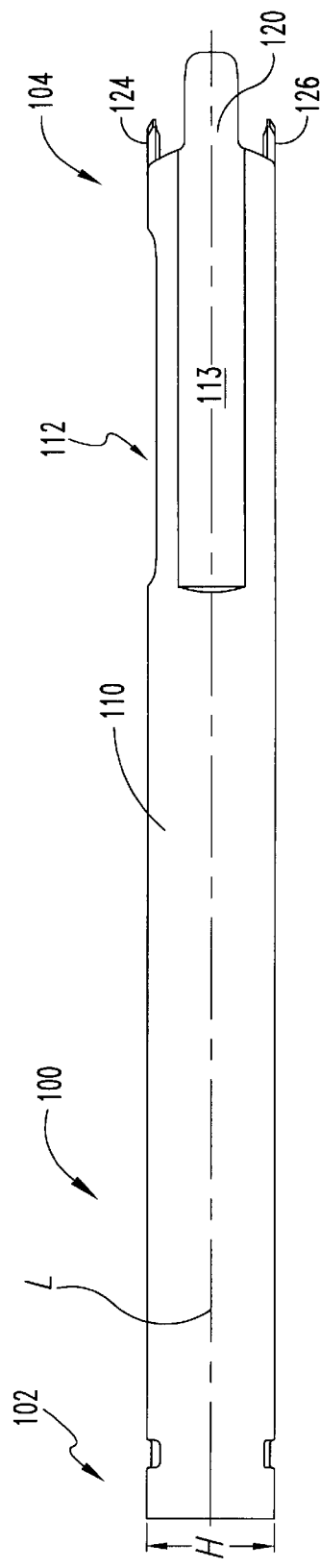
FIG. 5 is a side view of the guide sleeve of FIG. 3.

Referring to FIGS. 4 and 5, guide sleeve 100 is shown in front and side views, respectively, to further illustrate an additional aspect of the invention. A proximal end 102 the guide sleeve 100 has a maximum width W1. At distal end 104 of sleeve 100, wall 110 has a reduced wall thickness at side walls 114 and 113 defining a width W2 that is less than width W1. The side walls 113, 114 are preferably not entirely flat and have a slight curvature. Side walls 113, 114 provide a reduction in wall thickness of wall 110 and taper to the full wall thickness of wall 110 at the termination of side walls 113 and 114. The reduction in width of wall 110 decreases the amount of vasculature and neural tissue retraction in the area adjacent the disc space. The desirable reduction in width is accomplished with little reduction in the required strength of the device since distractors 50, 80 are used to distract and maintain the distraction of the vertebral bodies instead of the extensions or side flanges 118, 120 of guide sleeve 100.

Figure 9:
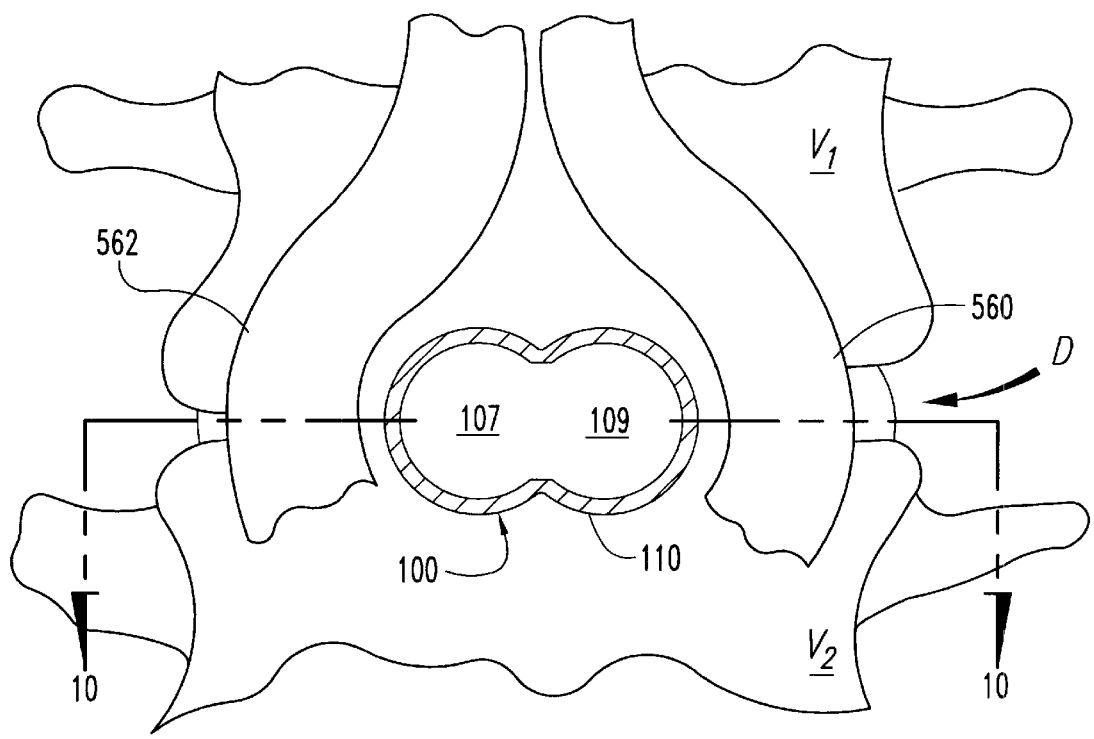
FIG. 9 is an anterior to posterior view of a guide sleeve assembly according to FIG. 3, the guide sleeve assembly is positioned in relation to a pair of adjacent vertebral bodies and blood vessels.

There are also shown in FIGS. 4 and 9 a first working channel portion 107, defined about axis L1, and a second working channel portion 109, defined about axis L2. These working channel portions 107, 109 are positioned on either side of longitudinal axis L of sleeve 100. There is no wall or other structure separating working channel portions 107 and 109. Working channel portion 107 is that portion of working channel 130 about axis L1 between longitudinal axis L and inside surface of 116 of guide sleeve 100. Similarly, working channel portion 109 is that portion of working channel 130 about axis L2 between longitudinal axis L and inside surface 116. Thus, working channel portions 107 and 109 are substantially equal in area, and each has a truncated circular shape, with the truncated portions of each working channel 107 and 109 positioned adjacent one another.

Figure 6:
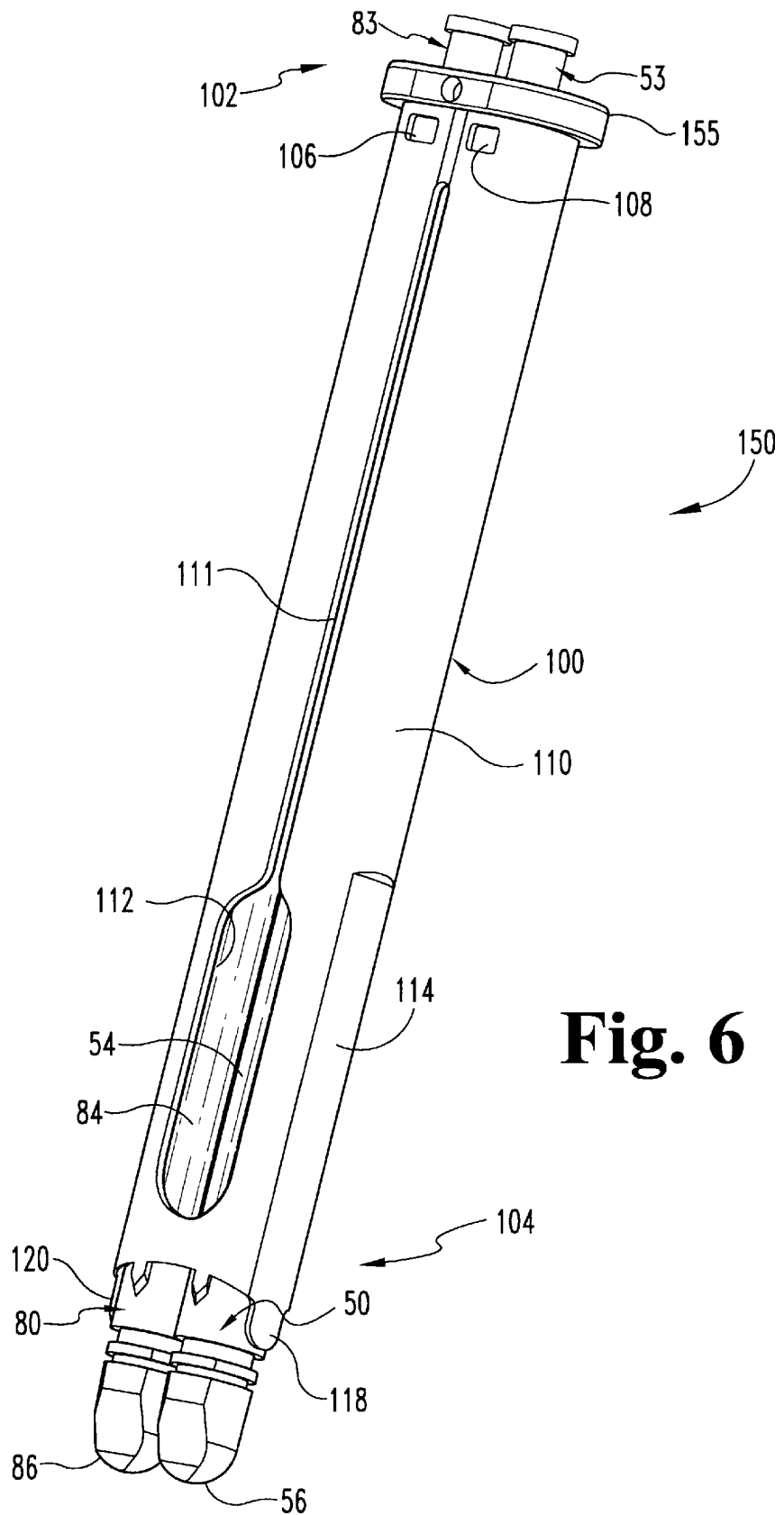
FIG. 6 is a perspective view of a guide sleeve assembly according to another aspect of the present invention.

Referring now to FIG. 6, there is illustrated a distractor/guide sleeve assembly 150 that includes distractors 50 and 80 disposed within working channel 130 of guide sleeve 100 in side-by-side relation. Distractors 50, 80 reside within sleeve 100 with each distractor substantially occupying all or a portion of a corresponding one of working channel portions 107 and 109 of working channel 130. Each distractor 50, 80 extends from proximal end 102 to distal end 104 of the guide sleeve 100. Flange ring 155 is in the form of a flange extending about the proximal end 102 of guide sleeve 100 and contacts a driving cap positioned on distractors 50, 80 in order to maintain the relative positioning between sleeve 100 and distractors 50, 80 during insertion of assembly 150.

Referring now to FIG. 7, there is illustrated an end view at distal end 104 of the assembly 150 showing distractors 50 and 80 in side-by-side relation. More particularly, shaft 54 of distractor 50 is received within concave portion 98 of distractor shaft 84. As also illustrated in this view, concave portion 96 of distractor tip 86 is coextensive with concave surface 98 to form a concave surface that extends the length of the distractor 80. The concave surface of distractor 80 has a radius of curvature R that is preferably about one half the diameter of the cage or implant to be inserted into the disc space. For example, an 18 mm diameter implant requires use of a distractor 80 having a radius of curvature R of about 9 mm.

When distractor 50 is removed from guide sleeve 100, there is defined a cylindrical working space through the working channel 130 adjacent and along the recessed areas of distractor 80. The cylindrical working space includes that portion of the working channel 130 between concave surfaces 96, 98 and inside wall 116 of the guide sleeve 100. Thus, the working space occupies substantially all of working channel portion 107, (FIG. 4) and a portion of working channel portion 109. The area of the portion of the working channel portion 109 occupied by the cylindrical working space is indicated in FIG. 7 by the hatched area A, and is hereinafter referred to as the overlap region. This overlap region A allows operative procedures to be performed in the working space adjacent the distractor 80 using conventionally sized tools and implements while providing a guide sleeve 100 of reduced overall width. The amount of width reduction achieved is approximately the maximum width of overlap region A. It should be understood that shaft 84 need not have a recessed area to provide a cylindrical working space in the disc space, but rather can be provided with a reduced diameter or size that maintains access to the overlap region A in the disc space.

Figure 8:
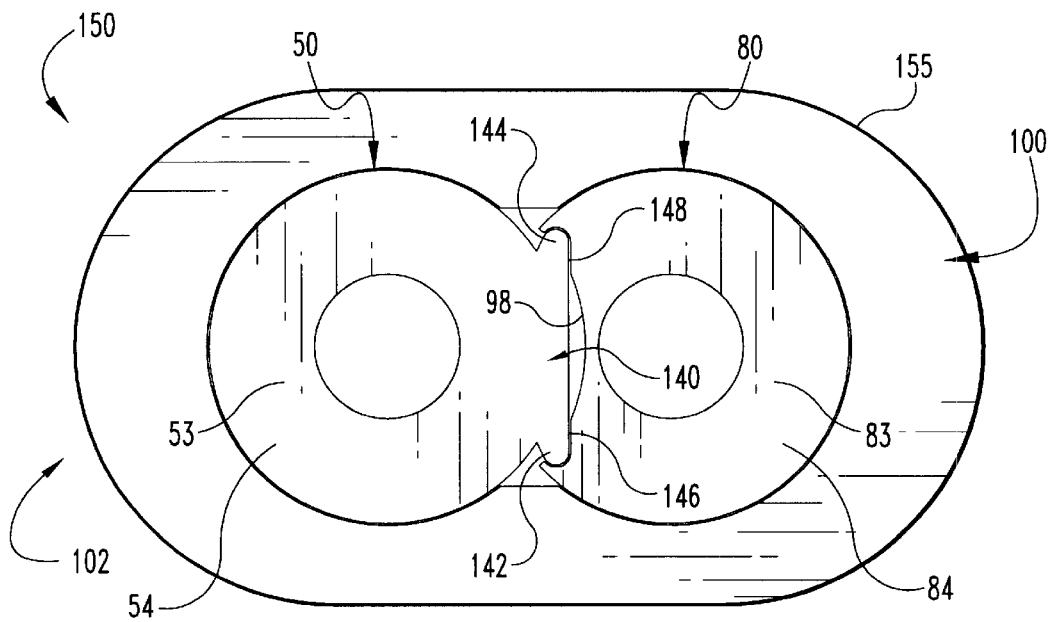
FIG. 8 is an enlarged end view of the proximal end of the guide sleeve assembly of FIG. 6.

In FIG. 8 there is shown a top view of the guide sleeve assembly 150, looking down on proximal ends 53, 83 of the distractors 50, 80 and the proximal end 102 of guide sleeve 100. In one embodiment, there is provided adjacent proximal end 53 of distractor 50 a locking segment 140 formed with and extending from the distractor shaft 54. Locking segment 140 has a first projection 142 and a second projection 144. First and second projections 142, 144 are received within corresponding notches 146, 148 defined in concave surface 98 of shaft 84 of distractor 80 to prevent rotation of distractors 50 and 80 with respect to one another. The present invention also contemplates other mechanisms for engaging distractors 50 and 80 to prevent rotation relative to one another as would occur to those of ordinary skill in the art. For example, the above described distractor clip 75 can be used to couple the distractors 50, 80 together. Moreover, it is contemplated that the distractors 50, 80 may be inserted without any locking mechanism.

The present invention contemplates that access to the disc space has heretofore been provided by known surgical techniques and therefore will not be further described herein. The use of intraoperative templates for providing access to the disc space is known in the art. One example of a procedure for gaining access to the disc space is disclosed in the '917 patent application. Another reference including techniques for template positioning and disc space distraction using a starter distractor to initially distract the disc space is the surgical technique brochure entitled *Reduced Profile Instrumentation* published in 1999 by Sofamor Danek, said brochure being incorporated by reference herein in its entirety (hereinafter the Danek brochure.) The present invention also contemplates the use and application of other procedures for gaining access to the disc space in conjunction with the procedures and instruments discussed below as would occur to those skilled in the art. The templates contemplated herein define the area necessary for placement of implants and instruments having a specific configuration and size. While in a preferred embodiment, templates are provided for cylindrical implants having diameters ranging from 16 mm to 24 mm, it is contemplated that other diameters of implant and templates for use therewith may be used and other shapes, such as, but without limitation, squares and rectangles.

Access to an anterior portion of the spinal column is achieved by known methods. Blood vessels, particularly the aorta, vena cava, and branches thereof are mobilized to provide space for bilateral implant placement. The template is inserted into the body and advanced until the pins are disposed adjacent a disc space. The circumference of the template is selected to correspond to the circumference needed for bilateral placement of a pair of implants. More specifically, the area of the template closely approximates the area needed for placement of the guide sleeve disclosed herein, such as that shown in FIG. 7. It is contemplated that a guide sleeve 100 need not necessarily be used, and tissue to the surgical site is retracted by other means while the disc space is distracted by distractors 50 and 80. The surgical procedures are then performed in the working space defined by the distractors 50, 80 as discussed below without use of a guide sleeve.

Figure 10:
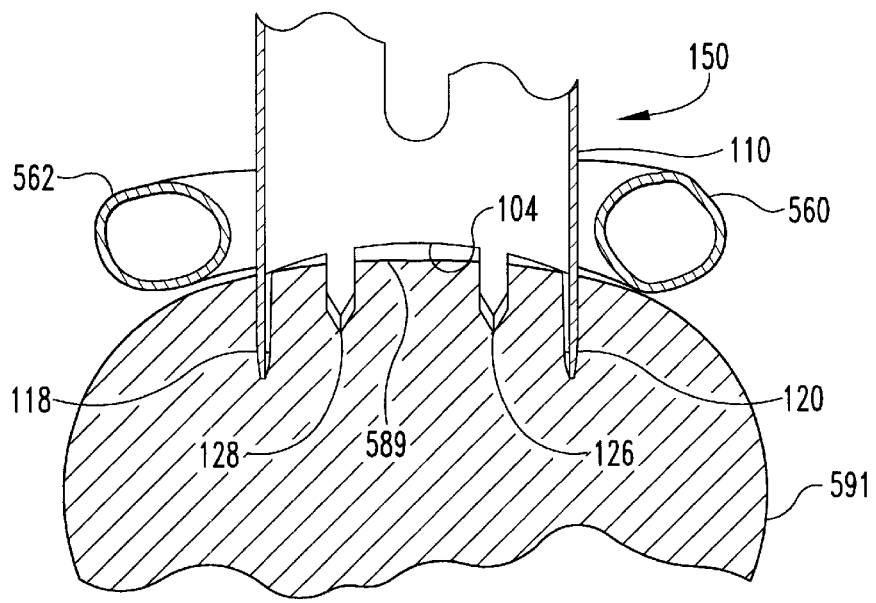
FIG. 10 is a partial cross-sectional view of the disc space through line 10—10 of FIG. 9.

Referring to FIG. 9, a cross section through guide sleeve 100, with distractors 50, 80 removed for clarity, is provided. Sleeve 100 is inserted into a disc space D between two adjacent vertebra V1 and V2. Disposed adjacent guide sleeve 100 are vessels 560 and 562 graphically representing portions of the aorta or vena cava. Referring to FIG. 10, a cross-section through line 10—10 of FIG. 9, sleeve 100, flanges 118, 120 on guide sleeve 100 extend into the disc space where the surgical procedures are being performed. Flanges 118, 120 and sleeve 100 inhibit contact between vessels and tissue surrounding the disc space and the tools used during the surgical procedure. Spikes 122, 124, 126, and 128 may be inserted into the bone of the corresponding vertebral body V1, V2.

Various tools and implements are usable with guide sleeve 100 including distractors 50, 80 disclosed herein and more specifically within the working spaces defined by the working channel 130 of guide sleeve 100. Several of these tools are disclosed in the Danek brochure and in the '917 patent application, while other tools are known to those skilled in the art to which the present invention relates.

Figure 11A:
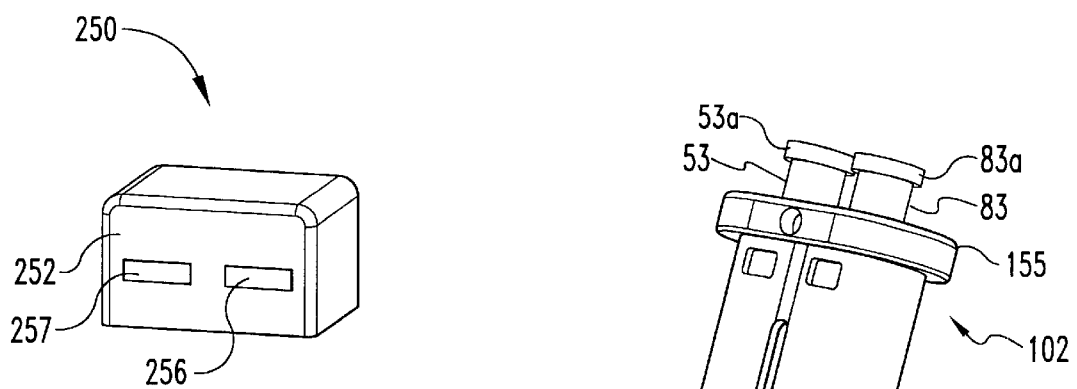
FIGS. 11a and 11b are front and rear elevation views, respectively, of a distractor driver cap for driving the distractors into the disc space.
Figure 11B:
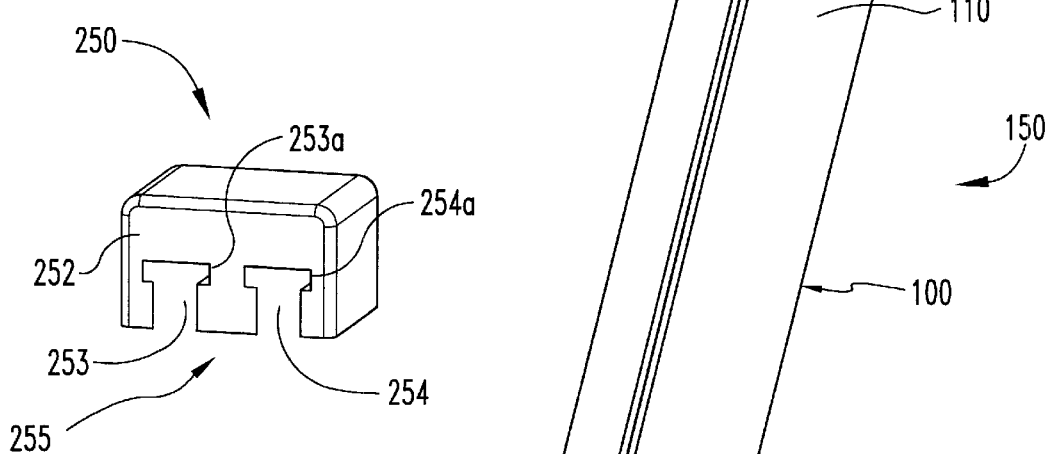
Figure 11:
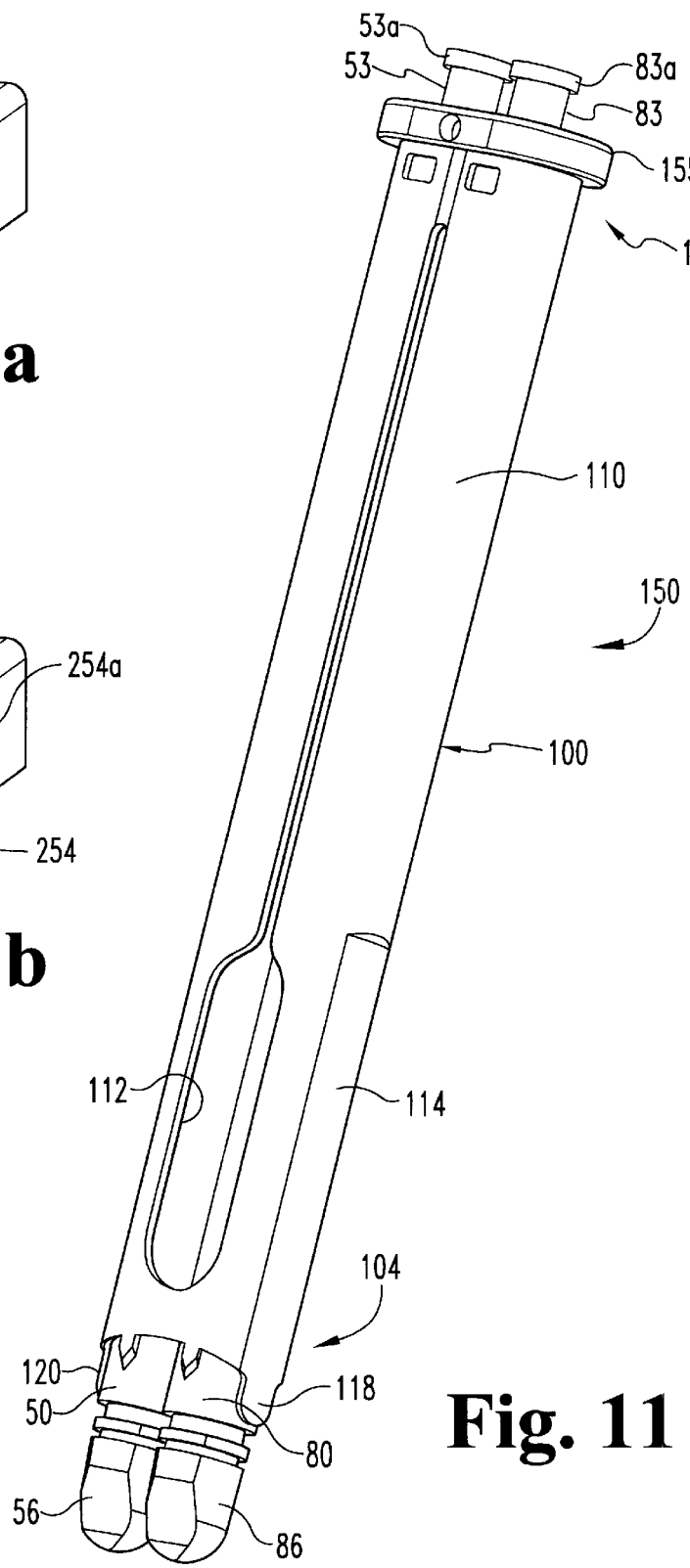
FIG. 11 is a perspective view of the guide sleeve assembly during insertion of the distractors into the disc space.

In accordance with a preferred method of using the apparatus of the present invention, reference will now be made to FIGS. 11 through 22. In FIG. 11, the sleeve assembly is assembled and prepared for insertion through the skin and to the disc space. Distractor driver cap 250 of FIGS. 11a and 11b is positioned on proximal end 53, 83 of distractors 50, 80. Driver cap 250 includes a body 252 having T-shaped slots 253 and 254 configured to receive flanged posts 53a and 83a of distractors 50 and 80, respectively. Opposite slots 253, 254 are windows 256 and 257. Preferably, the flanged portion of posts 53a and 83a extend into a corresponding one of the windows 256 and 257 and also into a corresponding one of the upper portions 253a and 254a of slots 253 and 254 to secure driver cap 250 to distractors 50, 80.

In use, distractor cap 250 contacts flange ring 155 with distractors 50, 80 in sleeve 100 such that distractor tips 56, 86 can be driven into the disc space while flanges 118, 120 remain positioned outside the disc space. The driving force applied to distractor cap 250 is transmitted to flange ring 155, and drives sleeve 100 towards the disc space along with distractors 50, 80. Alternatively, if distractors 50, 80 are not positioned in,guide sleeve 100, distractor cap 250 is secured to proximal ends 53, 83 and distractor tips 56, 86 are driven into the disc space. Distractor cap 250 is then removed and sleeve 100 placed over the inserted distractors 50, 80 and the procedure continues as discussed below. In this alternate technique, clip 75 may be used to couple distractors 50, 80 together during insertion. In a further variation, alternating insertion of distractors 50, 80 is not precluded by the present invention. However, insertion of distractors 50, 80 into the disc space simultaneously enables the surgeon maintain the positioning of distractors 50, 80 and control the depth of insertion of distractor tips 56, 86 with respect to one another.

Figures 12A, 12B, 13:
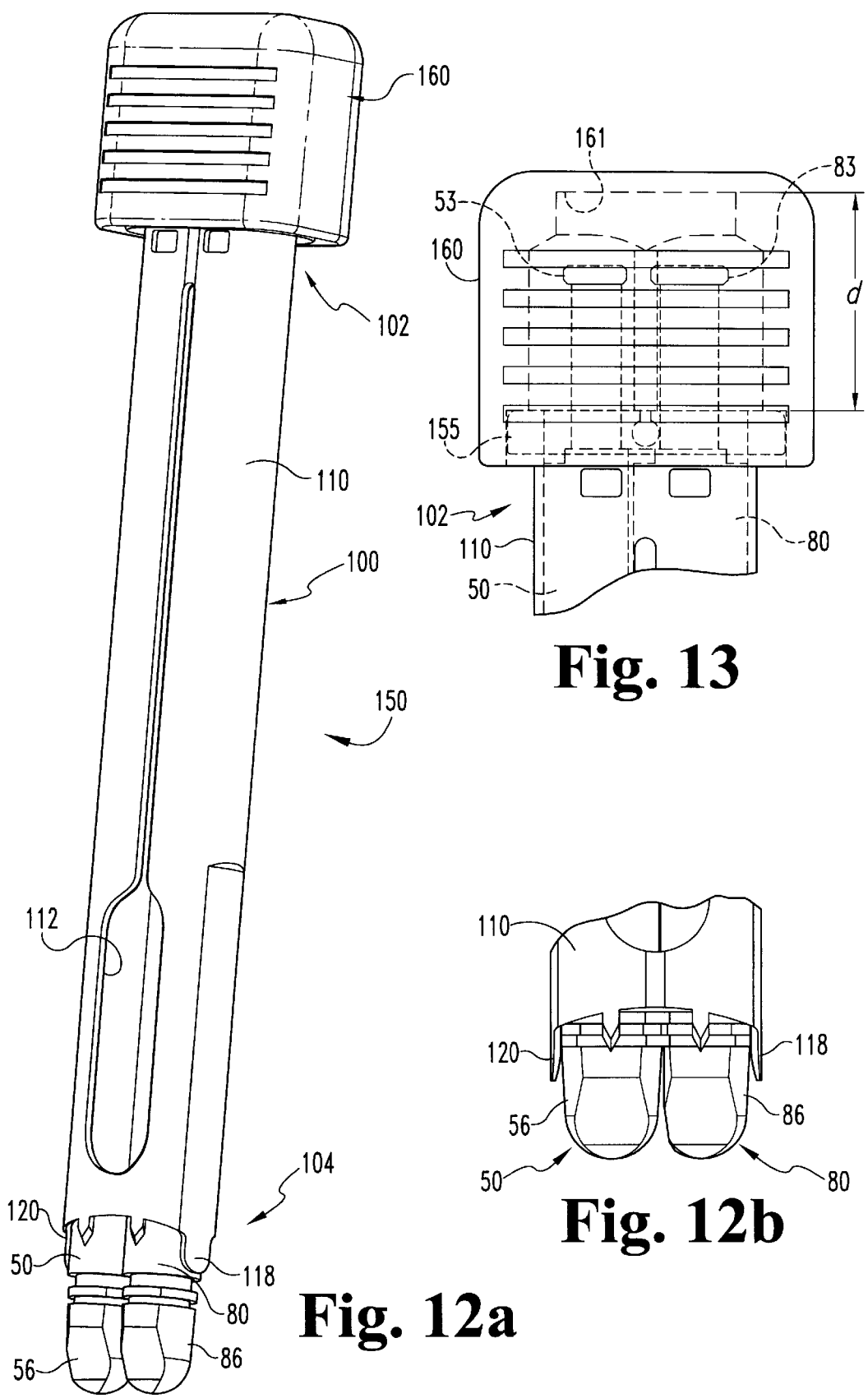
FIGS. 12a–12b are perspective views of the guide sleeve assembly 150 with an impactor cap disposed thereon prior to seating the guide sleeve.
FIGS. 13 is a perspective view of the guide sleeve assembly with an impactor cap disposed thereon.

In FIG. 12a, an impactor cap 160 is disposed about proximal end 102 of sleeve 100 over flange ring 155. Sleeve 100 is now relatively free to move with respect to distractors 50, 80. A driving force is applied to impactor cap 160 to drive sleeve 100 towards the disc space and position flanges 118 and 120 therein adjacent the distractor tips 56, 86 already positioned into the disc space as shown in FIG. 12b. Preferably, flanges 118 and 120 do not distract the disc space and prevent migration of tissue into the working space when distractor 50, 80 is removed from sleeve 100.

As shown in greater detail and enlarged FIG. 13, impactor cap 160 is positioned around and contacts the flange ring 155. Flange ring 155 is preferably of uniform size and shape for various sized guide sleeves 100, thus providing a modular attachment to each of the various sized guide sleeves for a single impactor cap 160. Impactor cap 160 has a hollow interior 161 for receiving proximal ends 53, 83. Hollow interior 161 has a depth d sufficient to allow movement of guide sleeve 100 into the disc space while the position of distractors 50, 80 is maintained.

In FIG. 14, a slap hammer 165 is engaged to distractor 50 in order to withdrawal distractor 50 from the disc space. In FIG. 15a the distractor 50 is removed from the working channel 130 of sleeve 110 using the slap hammer 165. The distractor tip 86 of concave distractor 80 remains disposed in the disc space to maintain the disc space distraction height during subsequent operative steps. In an alternate embodiment, it is contemplated that shaft 84 of distractor 80 is removably connected to tip 86, in which case the shaft may be withdrawn while leaving tip 86 in place. In a further embodiment, shaft 84 has a reduced size to accommodate insertion and rotation of devices into overlap region A of the disc space. With a removable or smaller diameter shaft, only tip 86 requires a recessed area.

In FIG. 15*b*, the withdrawn distractor 50 leaves a working space comprised of working channel portion 109 and an overlap portion, indicated by hatched area A. Thus, the concave surfaces 96, 98 of distractor 80 and inside surface 116 of sleeve 110 defines a substantially cylindrical working space for completion of further operative procedures as described further below. The working space defines a substantially circular cross section along guide sleeve 100 that is adapted for receiving surgical tools therethrough to prepare the disc space for insertion of an implant. The overlapping configuration of distractors 50, 80 provides a reduced overall width for guide sleeve 100.

Figure 16A:
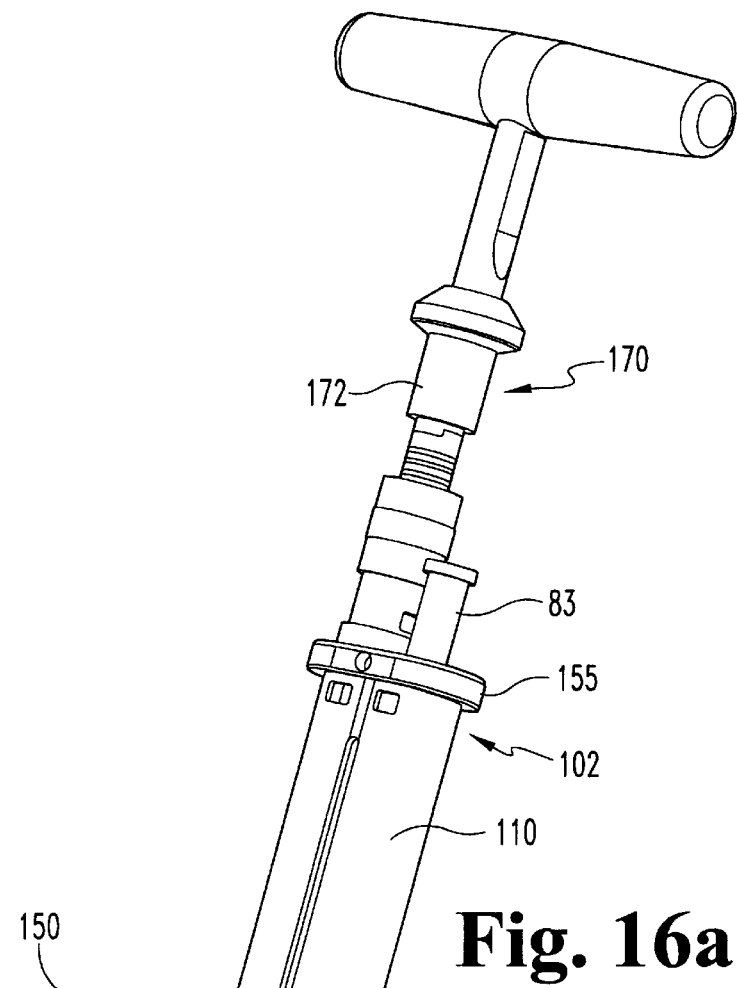
FIGS. 16a–16b are a perspective view and an end view, respectively, of the guide sleeve assembly with a reamer disposed adjacent a distractor.
Figure 16B:
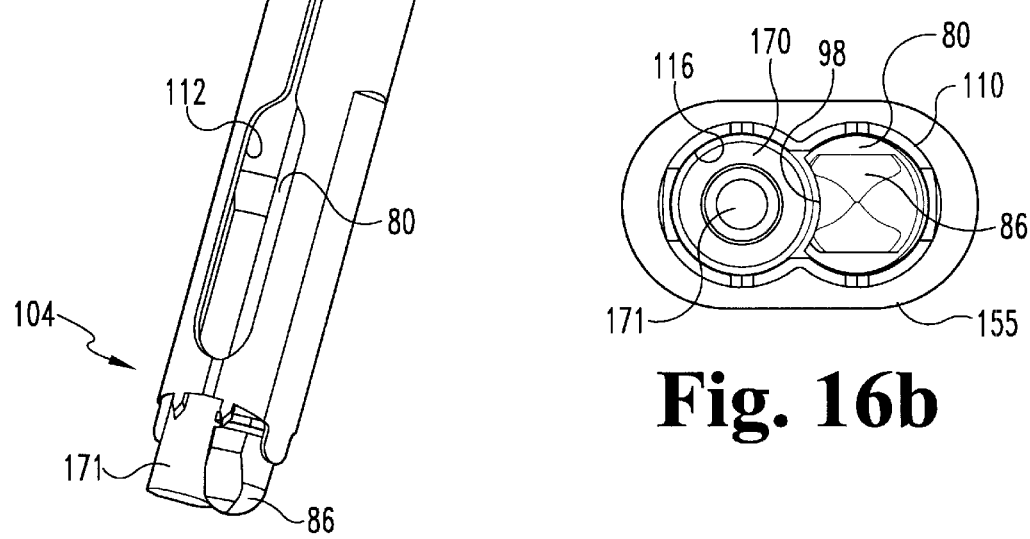

In FIGS. 16*a*–16*b*, there is shown a reamer 170 disposed through guide sleeve 110. A cutting head 171 has threads as known in the art to ream the disc space. As shown in FIG. 16*b*, reamer 170 is positioned within the working space adjacent distractor 80, while distractor tip 86 maintains the disc space distraction. Concave surface 98 of shaft 84 of distractor 80 and the inside surface 116 of sleeve 110 acts as a guide for insertion and/or withdrawal of reamer 170. The depth of reaming can be controlled with a depth stop 172 and verified via fluoroscopy In FIGS. 17*a*–17*c*, the reamer 170 is withdrawn and replaced by a tapping tool 175 with a head 176 to prepare the space for a threaded implant. As shown in FIGS. 17*b* and 17*c*, tapping tool 175 is positioned within the working space adjacent the concave distractor 80, while distractor tip 86 maintains the disc space distraction. The concave surface 98 of shaft 84 of distractor 80 and inside surface 116 of sleeve 110 acts as a guide for insertion of tapping tool 175. Tapping tool 175 has a depth stop 178 to control the tapping depth in the disc space. Depth and sagittal alignment can also be verified via fluoroscopy during tapping.

Figures 18A, 18B:
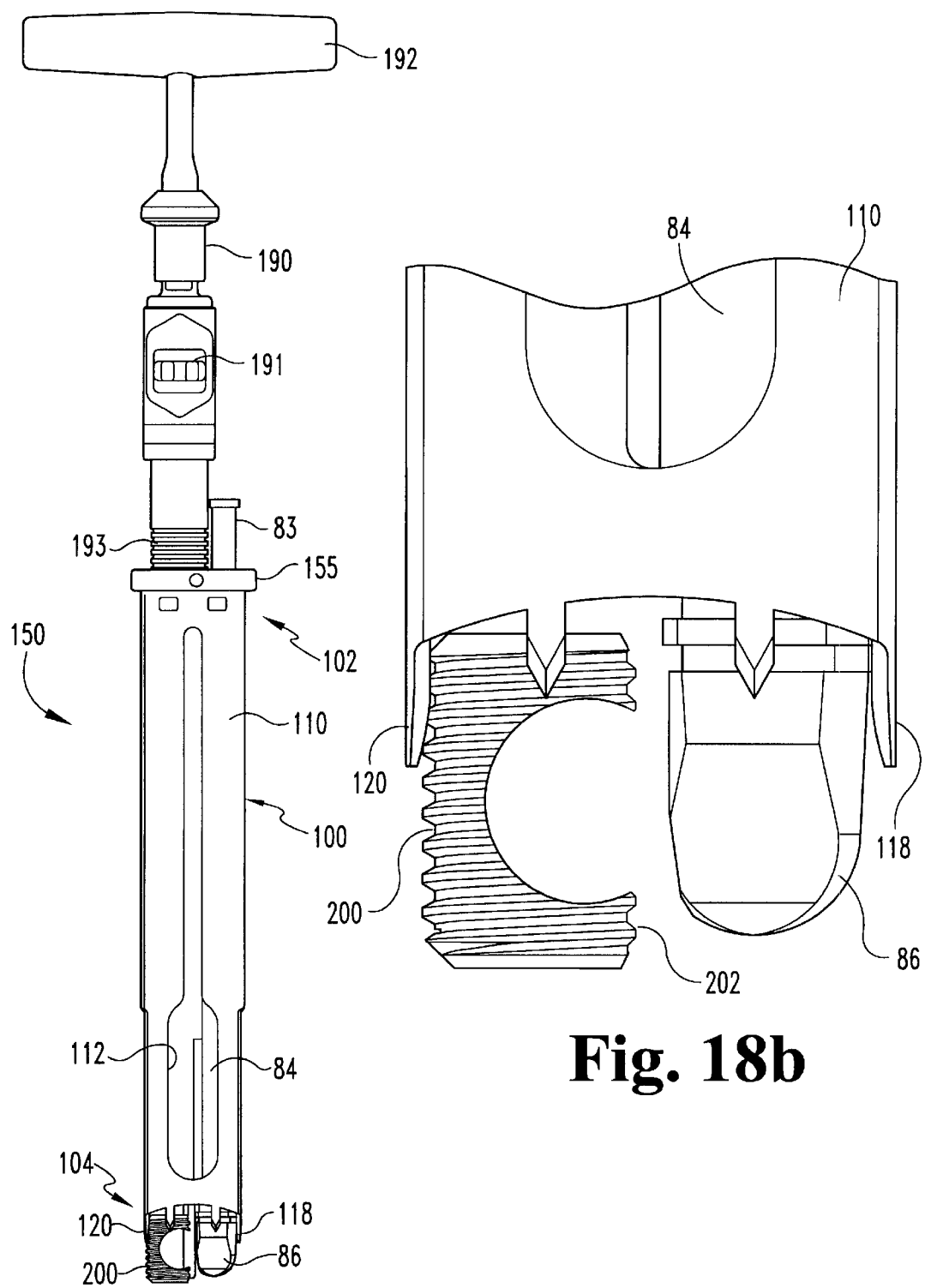
FIGS. 18a–18c are a perspective view, detail view and end view, respectively, of the guide sleeve assembly with an implant disposed adjacent a distractor.
Figure 18C:
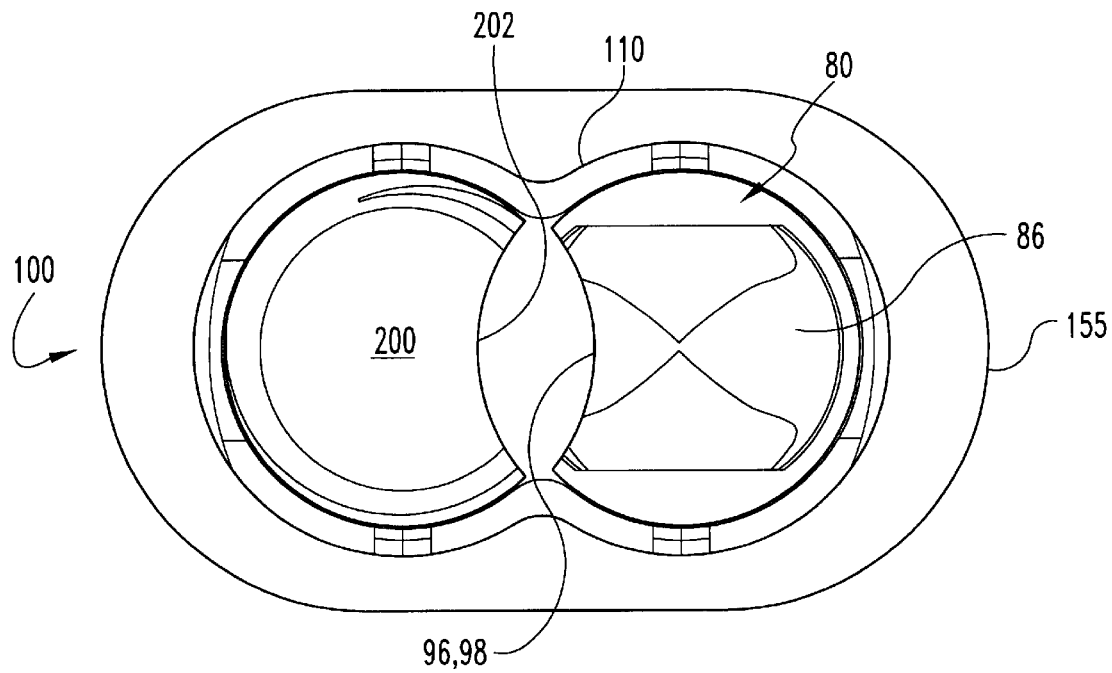

In FIGS. 18*a*–18*c*, the tapping tool 175 is withdrawn and replaced by an implant insertion device 190 with a threaded implant 200 engaged on a distal end thereof. Threaded implant 200 and insertion device 190 may be any one of the types and configuration disclosed in a first pending PCT Application No. PCT/US00/00590 filed on Jan. 11, 2000 and a second PCT Application No. PCT/US00/00604, also filed Jan. 11, 2000; each claiming priority to U.S. Provisional Application No. 60/115,388, filed Jan. 11, 1999, each of said above referenced PCT applications being incorporated by reference herein in its entirety. Further, the implants of the present invention may be any other known implant and insertion device, so long as at least one implant has at least one recessed side wall. The implants may be formed of any biocompatible material. Concave surface 98 of shaft 84 of distractor 80 arid inside surface 116 of sleeve 110 acts as a guide for insertion of the implant into the disc space.

Inserter 190 includes a thumbscrew 191 having a threaded shaft (not shown) extending through inserter 190 to couples implant 200 thereto via an internally threaded opening in a slotted end 201 (FIG. 19) of implant 200. T-handle 192 is used to rotate implant 200 and thread it into the disc space, as shown in the enlarged view of FIG. 18*b*. As shown more clearly in the enlarged view of FIG. 18*c*, implant 200 is inserted so that a concave face 202 is disposed toward concave surface 96 of distractor 80. This positioning of concave face 202 can be confirmed by providing alignment markings on insertion device 190 and sleeve 100. Further, insertion device 190 includes countersink marking 193 to provide an indication of the countersink of implant 200 into the disc space. To facilitate implant rotation, inserter 190 can be provided with a movable slide at its distal end that occupies the recessed area of concave surface 202 providing a round construct for threading. While implant 200 is threaded into place, distractor tip 86 maintains the disc space distraction.

Figures 19A, 19B, 19C:
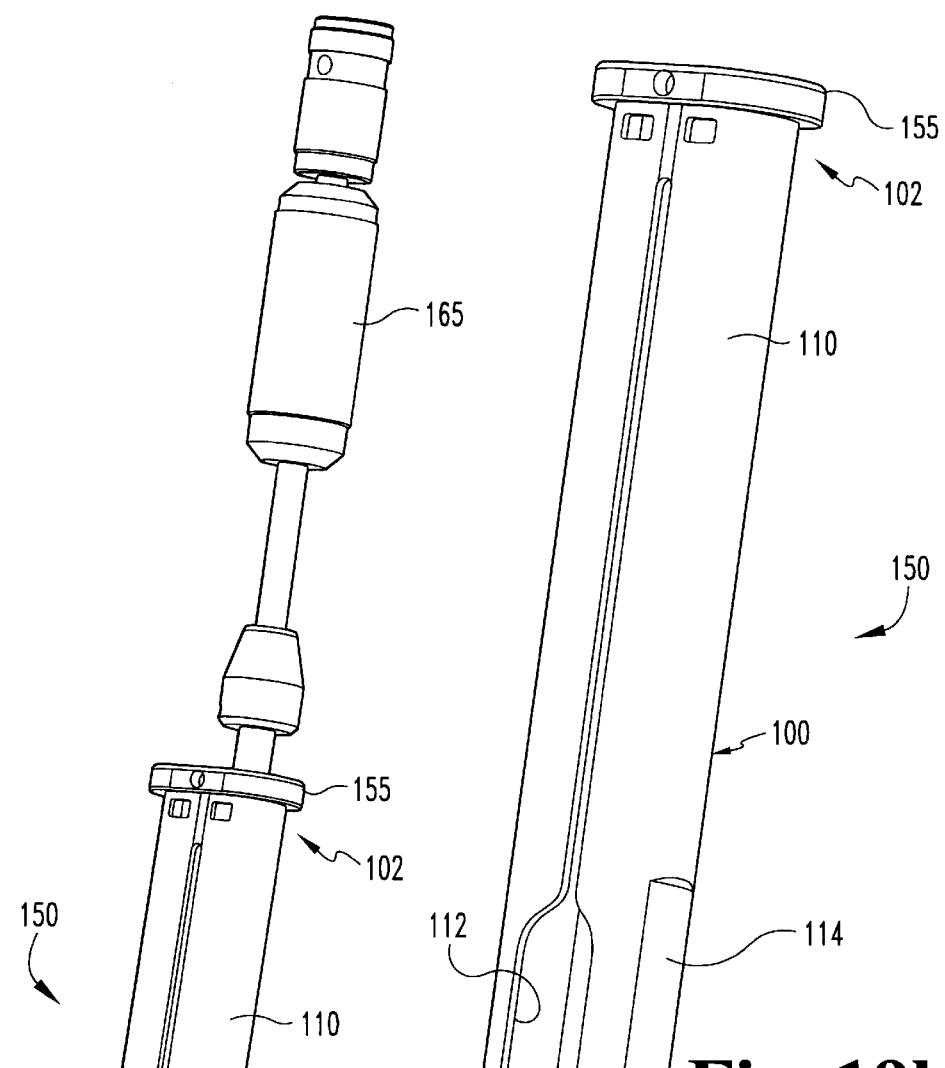
FIGS. 19a–19c are perspective views and an end view, respectively, of the guide sleeve assembly showing withdrawal of the other distractor.

In FIGS. 19*a*–19*b*, when implant 200 is placed in the desired position, and implant inserter 190 is removed from guide sleeve 100, distractor tip 86 is withdrawn from the disc space. Preferably, a slap hammer 165 is engaged to distractor 80 in order to withdraw distractor tip 86 from the disc space and distractor 80 from guide sleeve 100. As shown in FIGS. 19*b*–19*c*, distractor 80 is removed from working channel 130 of sleeve 110. Implant 200 remains disposed in the disc space to maintain the disc space distraction height during subsequent operative steps. The withdrawn distractor 80 leaves a working space comprised of working channel portion 107 and an overlap region A. Thus, concave surface 202 of implant 200 and inside surface 116 of sleeve 110 define a cylindrical working space in the disc space for further procedures as described below. The working space defines a circular cross section that is adapted for receiving conventionally sized surgical tools to prepare the disc space for insertion of a second implant adjacent implant 200, while providing a reduced overall width.

Figure 20A:
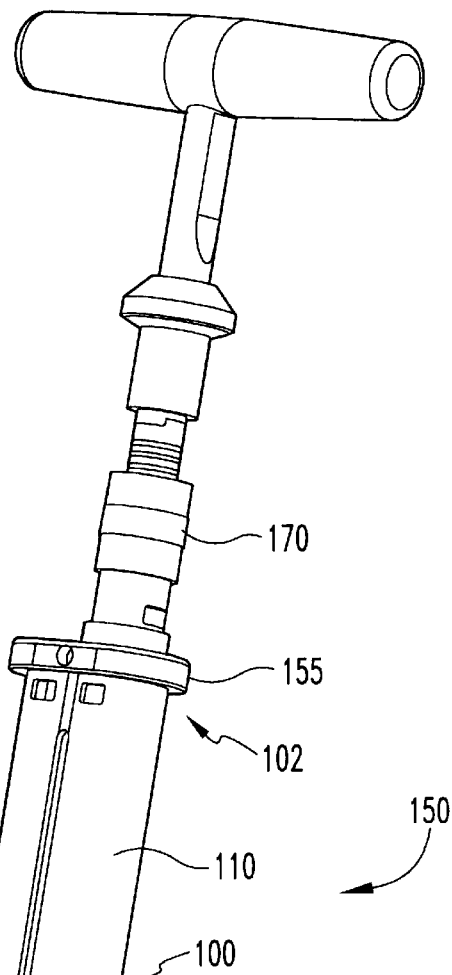
FIGS. 20a–20b are a perspective view and an end view, respectively, of the guide sleeve assembly with a reamer disposed adjacent an implant.
Figure 20B:
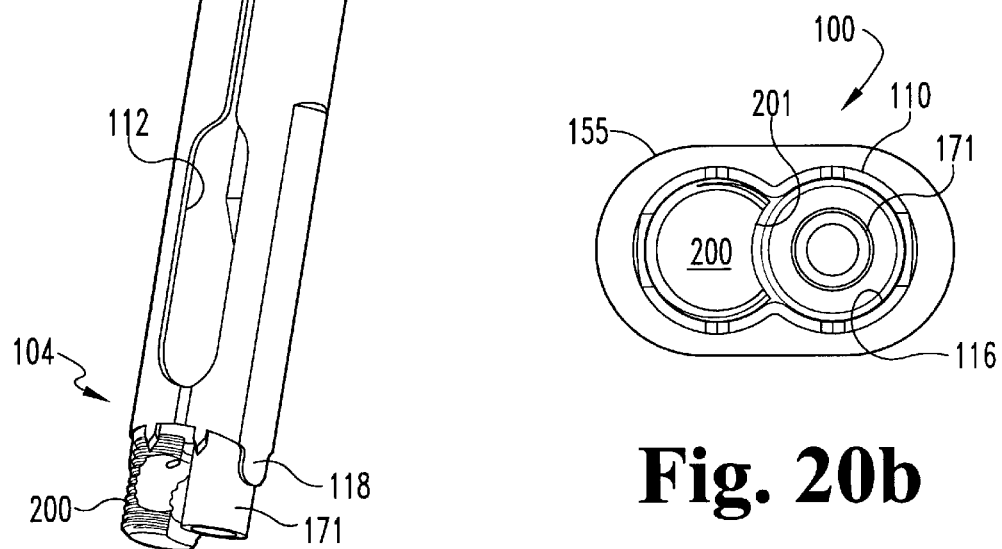
Figures 21A, 21B, 21C:
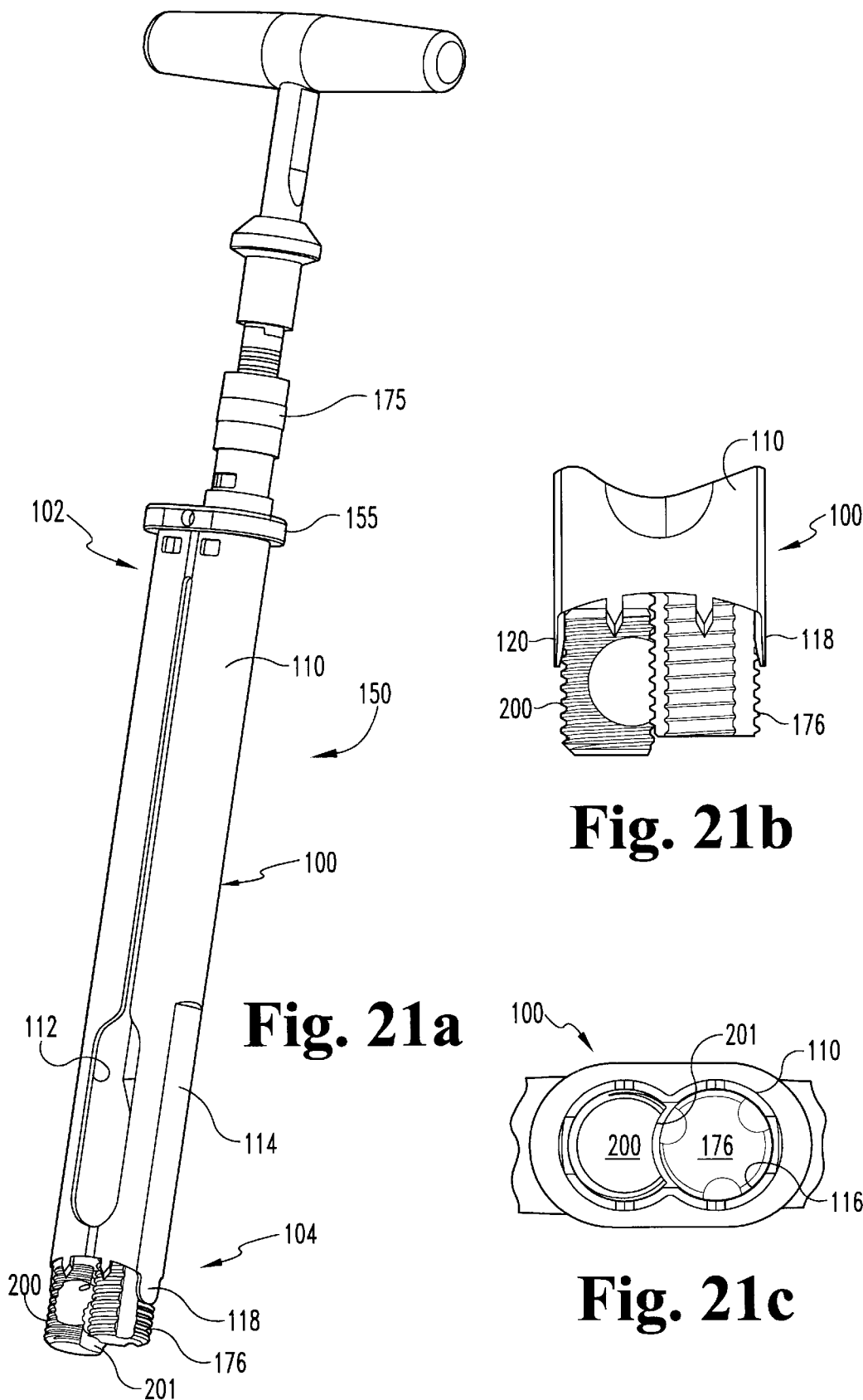
FIGS. 21a–21c are a perspective view, detail view and end view, respectively, of the guide sleeve assembly with a tap disposed adjacent an implant.

In FIGS. 20*a*–20*b*, the above described reamer 170 is disposed through guide sleeve 110. Cutting head 171 has threads as known in the art to ream the disc space. As shown in FIG. 20*b*, reamer 170 is positioned within the working space adjacent the concave surface 201 of implant 200, while implant 200 maintains the disc space distraction. The concave surface 201 of implant 200 and inside surface 116 of sleeve 110 acts as a guide for insertion and operation of reamer 170. In FIGS. 21*a*–21*c* reamer 170 is withdrawn and replaced by the above-described tapping tool 175 with head 176 to prepare the space for a second threaded implant. As shown in FIGS. 21*b* and 21*c*, head 176 of tapping tool 175 is positioned within the working space adjacent concave surface 201 of implant 200, while implant 200 maintains the disc space distraction. The concave surface 201 and inside surface 116 of sleeve 110 acts as a guide for insertion of tapping tool 175.

Figure 22C:
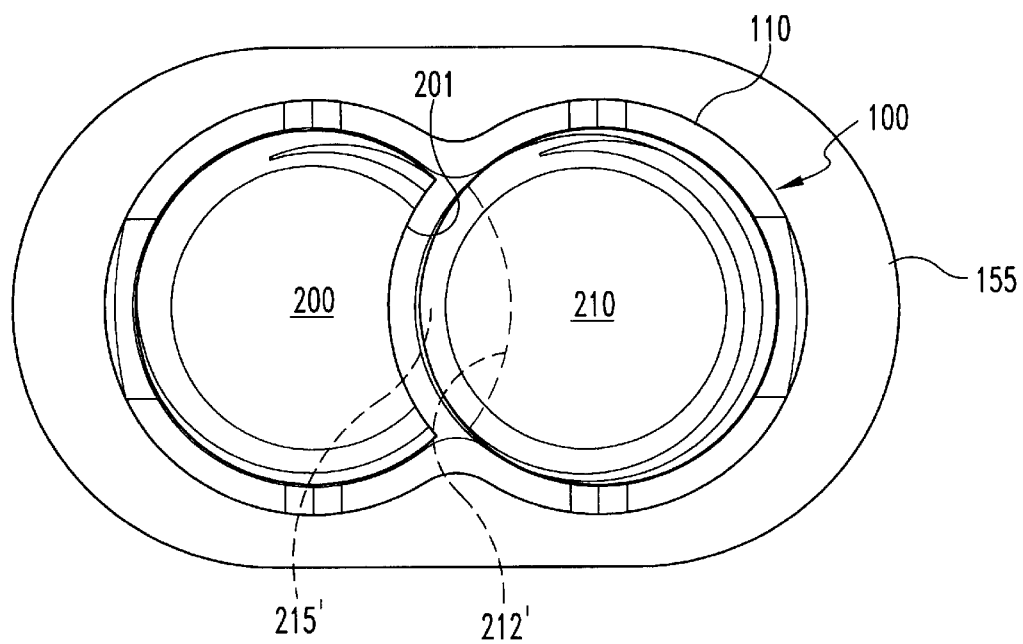
FIGS. 22a–22c are a perspective view, detail view and end view, respectively, of the guide sleeve assembly with an implant disposed adjacent an implant.
Figures 22A, 22B:
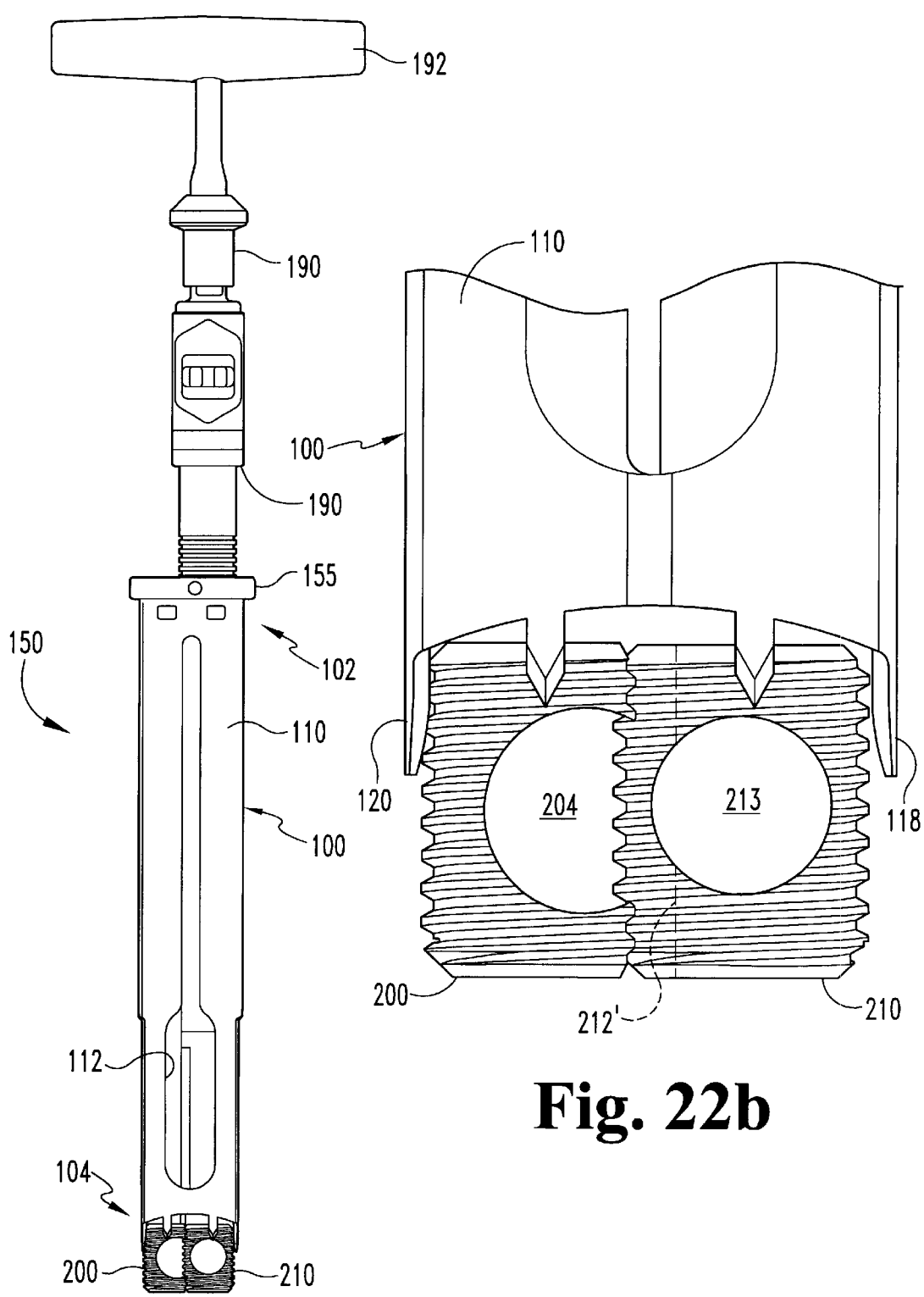

In FIGS. 22*a*–22*c*, the tapping tool is withdrawn and replaced by the above described implant insertion device 190, with a threaded implant 210 engaged on a distal end thereof. Threaded implant 210 may either have a circular cross-section, such as that shown in solid lines in enlarged FIGS. 22*b* and 22*c*, or have a cross-section identical to implant 200 with a concave surface 202 as shown in hidden lines. In either event, concave surface 201 of implant 200 acts as a guide for threading of implant 210 into the, disc space.

If an implant like that of implant. 200 is used, it is preferred to position implant 210 so that its concave surface 212' is disposed towards concave surface 202 of implant 200, forming a cavity 215' therebetween as indicated in dashed lines in FIG. 22*c*. The cavity may then be packed with bone growth promoting material. T-handle 192 is used to rotate implant 210 and thread it into the disc space, as shown in FIG. 22*b*, adjacent to implant 200. If a circular implant similar to that shown in FIG. 22*c* is used, implant 210 is nested within concave surface 201 of implant 200. Bone growth material can be placed in cavity 204 of implant 200 and in cavity 213 of implant 210.

While the use of threaded implants has been primarily discussed, the present invention likewise contemplates using push-in type implants and/or expandable implants in the disc space. Also, while it is preferred that the present invention be utilized for insertion of two implants at bilateral locations within the disc space, insertion of a single implant into the disc space is also contemplated herein.

Of course, the present invention makes use of depth stops and other devices for measuring and controlling the depth of the various procedures performed in the disc space. These devices and procedures are more fully explained in the Danek brochure and in the '917 patent application. Additionally, the present invention is not limited to use with the tools and instruments described above, and guide sleeve 100 and distractors 50, 80 may be used with other such devices as would normally occur to those skilled in the art to which the invention relates.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical instrument for distracting a spinal disc space, comprising:
   a distractor having a length and including:
   a shaft and a first distractor tip at a distal end of said shaft, said first
   distractor tip including:
   a first surface and an opposite second surface defining a distraction height;
   a recessed area extending between said first and second surfaces along at least a portion of said length; and
   a surface opposite said recessed area, wherein said distractor tip includes a width between said recessed area and said opposite surface sized to substantially occupy an implant insertion location of a generally cylindrical implant in the spinal disc space having a cross-sectional dimension at least as great as said distraction height.

2. The instrument of claim 1, wherein said shaft includes a recessed area adjacent to and coplanar with said recessed area of said distractor tip along a portion of a length of said shaft.

3. The instrument of claim 2, wherein said recessed area of said distractor tip and said recessed area of said shaft extend along substantially the entire length of said distractor.

4. The instrument of claim 2, wherein said recessed areas are concave surfaces.

5. The instrument of claim 1, wherein said recessed area is a concave surface.

6. The instrument of claim 1, wherein said first surface and said second surface are substantially parallel.

7. The instrument of claim 6, wherein said first surface and said second surface are each substantially planar.

8. The instrument of claim 1, wherein said recessed area is configured to permit rotation of a surgical device positioned adjacent thereto.

9. The instrument of claim 1, wherein said distractor tip is integrally formed with said shaft.

10. The instrument of claim 1, wherein said recessed area is a concave surface extending between said first and second surfaces.

11. The instrument of claim 10, wherein said opposite surface is a convex surface.

12. The instrument of claim 1, wherein said distractor tip includes a rounded leading end extending between said first and second surfaces.

13. The instrument of claim 1, wherein said distractor tip includes a rounded leading end and a pair of opposing inclined surfaces extending away from one another to respective ones of said first and second surfaces.

14. The instrument of claim 13, wherein said first surface and said second surface are substantially parallel.

15. The instrument of claim 14, wherein said first surface and said second surface are each substantially planar.

16. A surgical instrument for distracting a spinal disc space, comprising:
   a distractor having a length and including:
   a shaft and a first distractor tip at a distal end of said shaft, said distractor tip including:
   a first surface and an opposite second surface defining a distraction height;
   a recessed area extending between said first and second surfaces along at least a portion of said length;
   a surface opposite said recessed area, wherein said distractor tip includes a width between said recessed area and said opposite surface sized to substantially occupy an implant insertion location of a generally cylindrical implant in the spinal disc space having a cross-section dimension at least as great as said distraction height; and
   said shaft including a recessed area forming an extension of said recessed area of said distractor tip along another portion of said length.

17. The instrument of claim 16, wherein said recessed area of said distractor tip and said recessed area of said shaft extend along substantially the entire length of said distractor.

18. The instrument of claim 17, wherein said recessed areas are concave surfaces.

19. The instrument of claim 16, wherein said recessed areas are concave surfaces.

20. The instrument of claim 16, wherein said recessed areas are configured to permit rotation of a surgical device positioned adjacent thereto.

21. The instrument of claim 16, wherein said recessed areas are each formed by a concave surface extending between said first and second surfaces.

22. The instrument of claim 16, wherein said first distractor tip includes a rounded leading end and a pair of opposing inclined surfaces extending away from one another to respective ones of said first and second surfaces.

23. The instrument of claim 22, wherein said first surface and said second surface are substantially parallel.

24. The instrument of claim 22, wherein said first surface and said second surface are each substantially planar.

25. The instrument of claim 16, wherein said surface opposite said recessed area is a convex surface.

26. A surgical instrument for distracting a spinal disc space, comprising:
   a distractor having a length and including:
   a shaft and a first distractor tip at a distal end of said shaft, said distractor tip including:
   a first surface and an opposite second surface defining a distraction height;
   a concave surface extending between said first and second surfaces; and
   a surface opposite said concave surface, wherein said distractor tip includes a width between said concave surface and said opposite surface sized to substantially occupy an implant insertion location of a generally cylindrical implant in the spinal disc space having a cross-sectional dimension at least as great as said distraction height.

27. The surgical instrument of claim 26, wherein said shaft includes a concave surface forming an extension of said concave surface of said distractor tip.

28. The instrument of claim 27, wherein said concave surface of said distractor tip and said concave surface of said shaft extend along substantially the entire length of said distractor.

29. The instrument of claim 26, wherein said opposite surface is a convex surface.

30. The instrument of claim 26, wherein said first distractor tip includes a rounded leading end and a pair of opposing inclined surfaces extending away from one another to respective ones of said first and second surfaces.

31. The instrument of claim 30, wherein said first surface and said second surface are substantially parallel.

32. The instrument of claim 30, wherein said first surface and said second surface are each substantially planar.

* * * * *